(12) United States Patent
Chung et al.

(10) Patent No.: US 12,379,371 B2
(45) Date of Patent: Aug. 5, 2025

(54) IN VITRO TRANSCYTOSIS ASSAY

(71) Applicant: GENENTECH, INC., South San Francisco, CA (US)

(72) Inventors: Shan Chung, South San Francisco, CA (US); Van Hong Nguyen, South San Francisco, CA (US); An Song, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 1180 days.

(21) Appl. No.: 17/177,414

(22) Filed: Feb. 17, 2021

(65) Prior Publication Data

US 2021/0172932 A1    Jun. 10, 2021

Related U.S. Application Data

(63) Continuation of application No. PCT/US2019/046833, filed on Aug. 16, 2019.

(60) Provisional application No. 62/719,402, filed on Aug. 17, 2018.

(51) Int. Cl.
| | | |
|---|---|---|
| G01N 33/50 | (2006.01) | |
| C07K 16/32 | (2006.01) | |
| G01N 33/68 | (2006.01) | |

(52) U.S. Cl.
CPC ......... *G01N 33/5005* (2013.01); *C07K 16/32* (2013.01); *G01N 33/6854* (2013.01); *C07K 2317/24* (2013.01); *C07K 2317/526* (2013.01); *C07K 2317/71* (2013.01); *C07K 2317/72* (2013.01); *C07K 2317/92* (2013.01); *C07K 2317/94* (2013.01)

(58) Field of Classification Search
CPC ................ C07K 16/32; C07K 2317/24; C07K 2317/526; C07K 2317/71; C07K 2317/72; C07K 2317/92; C07K 2317/94; G01N 33/5005; G01N 33/6854; A61K 2800/49; A61K 8/11; A61K 8/35; A61K 8/922; A61Q 19/08

See application file for complete search history.

(56) References Cited

U.S. PATENT DOCUMENTS

| | | | |
|---|---|---|---|
| 2012/0282176 A1 | 11/2012 | Bohrmann et al. | |
| 2022/0033520 A1* | 2/2022 | Lazar | C07K 16/00 |
| 2024/0085404 A1* | 3/2024 | Liu | G01N 33/6854 |

FOREIGN PATENT DOCUMENTS

| | | |
|---|---|---|
| CN | 107533049 A | 1/2018 |
| WO | WO 2008/119096 A1 | 10/2008 |
| WO | WO 2012/048341 A1 | 4/2012 |
| WO | WO 2014/201273 A1 | 12/2014 |
| WO | WO 2015/031691 A1 | 3/2015 |
| WO | WO 2015/103339 A1 | 7/2015 |
| WO | WO 2015/164364 A2 | 10/2015 |
| WO | WO 2016/044227 A1 | 3/2016 |
| WO | WO 2016/118915 A1 | 7/2016 |
| WO | WO 2016/149418 A1 | 9/2016 |
| WO | WO 2016/160844 A2 | 10/2016 |
| WO | WO 2017/079593 A1 | 5/2017 |
| WO | WO 2018/058073 A2 | 3/2018 |
| WO | WO 2018/226293 A1 | 12/2018 |

OTHER PUBLICATIONS

Chung et al., "An in vitro FcRn-dependent transcytosis assay as a screening tool for predictive assessment of nonspecific clearance of antibody therapeutics in humans," mAbs, 2019, vol. 11, No. 5, pp. 942-955.*
Claypool et al., "Functional Reconstitution of Human FcRn in Madin-Darby Canine Kidney Cells Requires Co-expressed Human β2-Microglobulin," J. Biol. Chem., 2002, vol. 277, issue 31, pp. 28038-28050.*
Ober et al., "Differences in promiscuity for antibody-FcRn interactions across species: implications for therapeutic antibodies," International Immunol., 2001, vol. 13, issue 12, pp. 1551-1559.*
Caram-Salas et al., "In Vitro and In Vivo Methods for Assessing FcRn-Mediated Reverse Transcytosis Across the Blood-Brain Barrier," Methods in Molecular Biology, 763:383-400 (2011).
Castro Jaramillo et al., "Toward in vitro-to-in vivo translation of monoclonal antibody pharmacokinetics: Application of a neonatal Fc receptor-mediated transcytosis assay to understand the interplaying clearance mechanisms," MABS, 9(5):781-791 (2017).
Challa et al., "FcRn: From Molecular Interactions to Regulation of IgG Pharmacokinetics and Functions," Curr Top Microbiol Immunol, 382:249-272 (2014).
Cooper et al., "Efflux of monoclonal antibodies from rat brain by neonatal Fc receptor, FcRn," Brain Research, 1534:13-21 (2013).
Xu et al., "Advances in in Vitro Research Methods for The Metabolism of Bio-macro-molecular Drugs," Pharmaceutical and Clinical Research, No. 04, Aug. 15, 2018, 5 pgs.
Boswell et al., "Effects of Charge on Antibody Tissue Distribution and Pharmacokinetics," Bioconjug. Chem. 21:2153-2163 (2010).
Chaudhury et al., "The Major Histocompatibility Complex-related Fc Receptor for IgG (FcRn) Binds Albumin and Prolongs Its Lifespan," J. Exp. Med. 197:315-322 (2003).
Deng et al., "Pharmacokinetics of Humanized Monoclonal Anti-Tumor Necrosis Factor-α Antibody and Its Neonatal Fc Receptor Variants in Mice and Cynomolgus Monkeys," Drug Metab Dispos 38(4):600-605 (2010).

(Continued)

*Primary Examiner* — Galina M. Yakovleva
(74) *Attorney, Agent, or Firm* — Baker Botts L.L.P

(57) ABSTRACT

The present disclosure relates to methods and compositions useful for measuring the transcytosis of a molecule. In particular, the present disclosure relates to in vitro receptor-dependent transcytosis assays for evaluating the clearance rates of therapeutic antibody molecules and Fc-fusion proteins in humans and animals.

2 Claims, 6 Drawing Sheets

(56) References Cited

OTHER PUBLICATIONS

Dostalek et al., "Pharmacokinetic de-risking tools for selection of monoclonal antibody lead candidates," MAbs 9 (5):756-766 (2017).
Eaton et al., "Construction and Characterization of an Active Factor VIII Variant Lacking the Central One-Third of the Molecule," Biochemistry 25(26):8343-8347 (1986).
Fan et al., "Combinatorial labeling of single cells for gene expression cytometry," Science 347:1258367 (2015) 10 pgs.
Graham et al., "Characteristics of a Human Cell Line Transformed by DNA from Human Adenovirus Type 5," J. Gen Virol. 36:59-72 (1977).
Higel et al., "N-glycosylation heterogeneity and the influence on structure, function and pharmacokinetics of monoclonal antibodies and Fc fusion proteins," Eur J Pharm Biopharm 100:94-100 (2016).
Hotzel et al., "A strategy for risk mitigation of antibodies with fast clearance," MAbs 4(6):753-760 (2012).
Igawa et al., "Reduced elimination of IgG antibodies by engineering the variable region," Protein Eng Des Sel 23(5):385-392 (2010).
International Search Report mailed Jan. 27, 2020 in International Application No. PCT/US2019/048179.
Kenanova et al., "Tailoring the Pharmacokinetics and Positron Emission Tomography Imaging Properties of Anti-Carcinoembryonic Antigen Single-Chain Fv-Fc Antibody Fragments," Cancer Res 65(2):622-631 (2005).
Kim et al., "High Cleavage Efficiency of a 2A Peptide Derived from Porcine Teschovirus-1 in Human Cell Lines, Zebrafish and Mice," PLoS One 6(4):e18556 (2011) 8 pgs.
Lee et al., "Mannose Receptor-Mediated Regulation of Serum Glycoprotein Homeostasis," Science 295:1898-1901 (2002).
Lidington et al., "A comparison of primary endothelial cells and endothelial cell lines for studies of immune interactions," Transpl Immunol 7(4):239-246 (1999).
Mather et al., "Culture Of Testicular Cells In Hormone-Supplemented Serum-Free Medium," Annals N.Y. Acad. Sci. 383:44-68 (1982).
Mather, "Establishment and Characterization of Two Distinct Mouse Testicular Epithelial Cell Lines," Biol. Reprod. 23:243-251 (1980).
Milstein et al., "Hybrid hybridomas and their use in immunohistochemistry," Nature 305:537-540 (1983).
Roopenian et al., "FcRn: the neonatal Fc receptor comes of age," Nat Rev Immunol. 7(9):715-725 (2007).
Souders et al., "A novel in vitro assay to predict neonatal Fc receptor-mediated human IgG half-life," MAbs 7(5):912-921 (2015).
Srinivasan et al., "TEER Measurement Techniques for In-Vitro Barrier Model Systems," J Lab Autom 20(2):107-126 (2015).
Stefanich et al., "Evidence for an Asialoglycoprotein Receptor on Nonparenchymal Cells for O-Linked Glycoproteins," J Pharmacol Exp Ther 327(2):308-315 (2008).
Stockert et al., "The asialoglycoprotein receptor: relationships between structure, function, and expression," Physiol. Rev. 75:591-609 (1995).
Tao et al., "Studies of Aglycosylated Chimeric Mouse-Human IgG. Role of Carbohydrate in the Structure and Effector Functions Mediated by the Human IgG Constant Region," J Immunol 143(8):2595-2601 (1989).
Tesar et al., "Ligand Valency Affects Transcytosis, Recycling and Intracellular Trafficking Mediated by the Neonatal Fc Receptor," Traffic 7(9):1127-1142 (2006).
Urlaub et al., "Isolation of Chinese hamster cell mutants deficient in dihydrofolate reductase activity," Proc. Natl. Acad. Sci. USA 77:4216-4220 (1980).
Vugmeyster et al., "Pharmacokinetics and toxicology of therapeutic proteins: Advances and challenges," World J Biol Chem 3(4):73-92 (2012).
Ward et al., "Targeting FcRn for the modulation of antibody dynamics," Mol Immunol 67(2 Pt A):131-141 (2015).
Yadav et al., "Evaluating the Use of Antibody Variable Region (Fv) Charge as a Risk Assessment Tool for Predicting Typical Cynomolgus Monkey Pharmacokinetics," J Biol Chem 290(50):29732-29741 (2015).
Yamaura et al., "Functional Comparison of Human Colonic Carcinoma Cell Lines and Primary Small Intestinal Epithelial Cells for Investigations of Intestinal Drug Permeability and First-Pass Metabolism," Drug Metab Dispos 44(3):329-335 (2016).
Yeung et al., "A Therapeutic Anti-VEGF Antibody with Increased Potency Independent of Pharmacokinetic Half-life," Cancer Res 70(8):3269-3277 (2010).
Yu et al., "Production, characterization and pharmacokinetic properties of antibodies with N-linked Mannose-5 glycans," MAbs 4(4):475-487 (2012).
Cui et al., "Design of Clinical Pharmacokinetic Trials for Special Drug Delivery Systems," Peking Union Medical College Press, pp. 186-187, published on Jul. 31, 2018 [with English translation].

* cited by examiner

IN VITRO TRANSCYTOSIS ASSAY

CROSS-REFERENCE TO RELATED APPLICATIONS

This Application is a Continuation of International Patent Application No. PCT/US19/46833, filed Aug. 16, 2019, which claims priority to U.S. Provisional Patent Application Ser. No. 62/719,402, filed Aug. 17, 2018, the contents of each of which are incorporated by reference in their entirety, and to each of which priority is claimed.

FIELD OF INVENTION

The present disclosure relates to methods and compositions useful for measuring the transcytosis of a molecule. In particular, the present disclosure relates to in vitro receptor-dependent transcytosis assays for evaluating in vivo pharmacokinetic profiles, e.g., clearance rates, and/or half-lives of molecules that interact with FcRn, e.g., therapeutic antibodies, Fc fusion molecules, and molecules linked to albumin.

BACKGROUND

Therapeutic monoclonal antibodies (mAbs) have become a major class of pharmaceutical products worldwide due to their proven effectiveness in the treatment of a variety of diseases and their desirable pharmacological properties. One of the favorable pharmacological properties of mAb drugs is their typically long circulating half-life. Extended half-life of biotherapeutic products could allow less frequent dosing and/or lower dose of the drug which reduces cost of care, improves patient compliance, and lower concentration-dependent cytotoxicity/adverse events.

Significant progress has been made in understanding pharmacokinetics (PK) profiles of mAb drugs in animals and humans. Whereas many mAb drugs exhibit similar PK behavior that is analogous to endogenous IgG, substantial heterogeneity in non-specific clearance rate of mAb drugs in human are commonly observed. Therefore, evaluation and selection of clinical candidates for desirable PK properties is an important early step during drug development. A broad range of technologies involving in silico, in vitro and in vivo analyses have been employed to evaluate and/or predict PK behavior of mAbs in humans (Dostalek et al., 2017, MAbs 9 (5): 756-766). However, translation of PK data from animal to humans, and from in vitro assays to in vivo readouts remains elusive to drug developers (Vugmeyster et al., 2012, World J Biol Chem 3 (4): 73-92). In addition, while some animal models such as human FcRn transgenic mice (Avery, 2010) and non-human primate (Deng et al., 2011, Drug Metab Dispos 38 (4): 600-605) have been successfully used to project human PK of mAbs, these studies are typically time-consuming, costly, and involve animal sacrifice.

There are many complexities in predicting human PK of mAbs from animal studies and in vitro assays. Target-mediated drug disposition (TMDD) is known to impact dose-dependent PK behavior of mAbs resulting in nonlinear distribution and elimination. In the absence of TMDD, mAbs are expected to exhibit linear elimination and non-specific clearance rate which reflects target-independent molecule-specific drug catabolismthe non-specific clearance of mAbs is mediated mostly by lysosomal degradation in the reticuloendothelial system where the neonatal Fc receptor (FcRn)-mediated savage pathway plays a major role. Structurally, FcRn is a heterodimer composed of a transmembrane heavy chain (FCGRT) homologous to major histocompatibility complex (MHC) class-I like molecules and a soluble light chain, β2 microglobulin (B2M). FcRn binds to the Fc domain of endogenous IgG at acidic pH (less than 6.5), but only minimally at neutral or basic pH (greater than 7.0). This unique property allows FcRn to protect Fc-containing molecules from degradation by binding to them in acidic endosomes after their uptake into cells and then transport them back to the cell surface and release them to the circulation at physiological pH. In contrast, internalized molecules that are not bound to FcRn are directed to lysosomes for degradation (see FIG. 6 and Roopenian et al., Nat Rev Immunol. 2007 September; 7 (9): 715-25).

While the contribution of FcRn in prolonging half-lives of Fc-containing proteins is well recognized (Ward, 2015), reports of a lack of correlation between FcRn binding and PK for mAb drugs in human (Suzuki, 2010; Zheng, 2011; Hotzel, 2012) suggests that binding affinity to FcRn is not the sole determinant for the elimination rate of Fc-containing proteins. Given the function of FcRn in intracellular trafficking, the dynamics of endosomal sorting and trafficking of Fc-containing molecule/FcRn complexes are likely to impact overall efficiency of the FcRn-mediated salvage mechanism and hence the molecule's non-specific clearance rate. In addition, the processes of cellular uptake via pinocytosis or endocytosis as well as degradation in lysosome could also play a role in determining the rate and extent of mAb degradation (Gurbaxani, 2013). Lastly, biochemical characteristics such as charge/pI and glycosylation patterns have been reported to impact mAb disposition (Datta-Mannan, 2015; Igawa, 2010; Khawli, 2010). These molecular characteristics may in themselves influence mAb structure so as to alter the "true" interaction with FcRn in vivo or may contribute to nonspecific cell surface binding that alters the mode/rate of internalization and the relative proportion of FcRn-mediated intracellular trafficking pathways including recycling and transcytosis.

A variety of in vitro assays have been developed to model IgG Fc-FcRn interactions. An intrinsic limitation of many of these assays is the absence of non-specific interactions that involves cells, plasma proteins, and extracellular matrix (ECM) components, and the intracellular trafficking parameters associated with recycling, transcytosis, and lysosomal degradation of mAbs. Preferably, an in vitro assay for the prediction of mAb clearance would be capable of assessing the combined effects of electrostatic interactions, cellular uptake of Abs, interactions with FcRn, and intracellular trafficking of the molecules. However, given the multiple factors that influence mAb disposition in vivo, it is difficult to develop a simple in vitro assay that accurately and consistently predicts PK behavior of mAb drugs.

Development of animal models likewise present challenges. While animal models such as human FcRn transgenic mice (Avery, 2010) and non-human primate (Deng, 2011) models have been successfully used to project human PK of mAbs, these studies are typically time-consuming, costly, and involve animal sacrifice. Furthermore, translation of PK behavior from animal studies to humans is not straightforward, in part due to species differences in FcRn binding, TMDD, and induction of anti-drug immune responses (Liu, 2018).

There thus remains a need for methods to predict the in vivo PK properties (e.g., clearance or half-life) of therapeutic molecules that can be conducted in a short amount of time and at reasonable cost to aid in evaluation and selection of therapeutic molecules.

SUMMARY OF THE INVENTION

The present disclosure relates to methods and compositions useful for measuring the transcytosis of a molecule of interest. In particular, the present disclosure relates to in vitro receptor-dependent transcytosis assays for evaluating in vivo pharmacokinetic profiles, e.g., clearance rates, and/or half-lives of molecules that interact with FcRn, e.g., therapeutic antibodies, Fc fusion molecules, and molecules linked to albumin.

In certain embodiments, the present disclosure is directed to methods for determining a pharmacokinetic (PK) parameter of a molecule of interest. For example, such methods can comprise determining a measure of transcytosis of the molecule or a plurality of molecules through a cell or a plurality of cells under conditions of physiological pH. In certain embodiments, the PK parameter is a measure of in vivo clearance of the molecule. In certain embodiments, the PK parameter is a measure of the in vivo half-life of the molecule.

In certain embodiments, the measure of transcytosis used in connection with the methods disclosed herein, is the rate of transcytosis. In certain embodiments, the measure of transcytosis is a measure of the amount of the molecule or molecules that are transcytosed.

In certain embodiments, the measure of transcytosis is determined by measuring the transcytosis of the molecule or molecules from a solution in a first chamber to a solution in a second chamber, wherein the first and second chamber are separated by a cell monolayer and the solution in each chamber is at physiological pH. In certain embodiments, the cell or a plurality of cells are Madin-Darby Canine Kidney (MDCK) cells. In certain embodiments, the cells comprise at least one heterologous gene. In certain embodiments, the at least one heterologous gene is selected from the group consisting of a FCGRT gene and a B2M gene. In certain embodiments, the cells express a heterologous cell surface protein. In certain embodiments, the heterologous cell surface protein comprises a neonatal Fc receptor (FcRn). In certain embodiments, measuring the transcytosis of the molecule comprises the use of an enzyme-linked immunosorbent assay (ELISA), liquid-scintillation counting (LSC), quantitative PCR, or a fluorescence reader system. In certain embodiments, the methods disclosed herein further comprise: determining the in vivo clearance of the molecule based on the number of molecules measured.

In certain embodiments of the present disclosure, the molecule of interest is a molecule that naturally binds to FcRn. In certain embodiments, the molecule is engineered to bind FcRn. In certain embodiments, the molecule is an Fc-containing molecule. In certain embodiments, the Fc-containing molecule is a receptor Fc fusion molecule. In certain embodiments, the molecule is an antibody. In certain embodiments, the antibody is a monoclonal antibody. In certain embodiments, the molecule is an albumin-containing molecule.

In certain embodiments, the present disclosure is directed to a method for measuring the transcellular transportation of a plurality of a single molecule or a plurality of distinct molecules, comprising: a) introducing the plurality of a single molecule or the plurality of distinct molecules into a first of two chambers where the first chamber is separated from the second chamber by a cell or plurality of cells, and wherein each of the first and second chambers has a physiological pH value; and b) measuring the number of molecules transcytosed from the first chamber to the second chamber. In certain embodiments, the first chamber comprises a monolayer of cells. In certain embodiments, the cells are Madin-Darby Canine Kidney (MDCK) cells. In certain embodiments, the cells comprise at least one heterologous gene. In certain embodiments, the at least one heterologous gene is selected from the group consisting of a FCGRT gene and a B2M gene. In certain embodiments, the cells express a heterologous cell surface protein. In certain embodiments, the heterologous cell surface protein comprises a neonatal Fc receptor (FcRn). In certain embodiments, measuring the number of the transcellularly transported molecules comprises the use of an enzyme-linked immunosorbent assay (ELISA), liquid-scintillation counting (LSC), quantitative PCR, or a fluorescence reader system. In certain embodiments, the methods disclosed herein further comprise: determining the in vivo clearance of the molecule based on the number of molecules measured.

In certain embodiments, the present disclosure is directed to methods of determining the in vivo clearance of a molecule, comprising: a) introducing the molecule into a first of two chambers where the first chamber is separated from the second chamber by a cell or plurality of cells, and wherein each of the first and second chambers has a physiological pH value; b) measuring the number of molecules transcytosed from the first chamber to the second chamber; and c) determining the in vivo clearance of the molecule based on the number of molecules measured. In certain embodiments, the first chamber comprises a monolayer of cells. In certain embodiments, the cells are MDCK cells. In certain embodiments, the cells comprise at least one heterologous gene. In certain embodiments, the at least one heterologous gene is selected from the group consisting of a FCGRT gene and a B2M gene. In certain embodiments, the cells express a heterologous cell surface protein. In certain embodiments, the heterologous cell surface protein comprises a neonatal Fc receptor (FcRn). In certain embodiments, measuring the number of the transcellularly transported molecule comprises the use of an enzyme-linked immunosorbent assay (ELISA), liquid-scintillation counting (LSC), quantitative PCR, or a fluorescence reader system. In certain embodiments, the molecule is a molecule that naturally binds to FcRn.

In certain embodiments, the present disclosure is directed to an assay for measuring the transcellular transportation of a plurality of molecules. For the example, but not by way of limitation, the assay can comprise employing a first chamber and a second chamber, each of the first and second chambers having a physiological pH value, wherein the first chamber receives a plurality of molecules, is configured to transcellularly transport the molecules to the second chamber, and the transcellular transportation of the plurality of molecules is measured. In certain embodiments, the first chamber comprises a monolayer of cells. In certain embodiments, the cells are MDCK cells. In certain embodiments, the cells comprise at least one heterologous gene. In certain embodiments, the at least one heterologous gene is selected from the group consisting of a FCGRT gene and a B2M gene. In certain embodiments, the cells express a heterologous cell surface protein. In certain embodiments, the heterologous cell surface protein comprises a neonatal Fc receptor (FcRn). In certain embodiments, measuring the number of the transcellularly transported molecules comprises use of an enzyme-linked immunosorbent assay (ELISA), liquid-scintillation counting (LSC), quantitative PCR, or a fluorescence reader system. In certain embodiments, the assay further comprises: determining the in vivo clearance of the molecules based on the number of molecules measured.

In certain embodiments, the present disclosure is directed to an assay system comprising: a first chamber and a second chamber, wherein each of the first and second chambers has a physiological pH; a monolayer of cells positioned in the first chamber such that the cells can mediate the transcytosis of a molecule introduced into the first chamber to the second chamber; and a detector for detecting the presence of a molecule in the second chamber. In certain embodiments, the cells are MDCK cells. In certain embodiments, the cells comprise at least one heterologous gene. In certain embodiments, the at least one heterologous gene is selected from the group consisting of a FCGRT gene and a B2M gene. In certain embodiments, the cells express a heterologous cell surface protein. In certain embodiments, the heterologous cell surface protein comprises a neonatal Fc receptor (FcRn). In certain embodiments, measuring the number of the transcellularly transported molecules comprises use of an enzyme-linked immunosorbent assay (ELISA), liquid-scintillation counting (LSC), quantitative PCR, or a fluorescence reader system.

BRIEF DESCRIPTION OF THE DRAWINGS

FIG. 2A shows flow cytometry histograms of cell surface expression of B2M for WT and 305-6 cells. FIG. 2B shows flow cytometry histograms of cell surface expression of FCGRT for WT and 305-6 cells.

DETAILED DESCRIPTION

Figure 1:
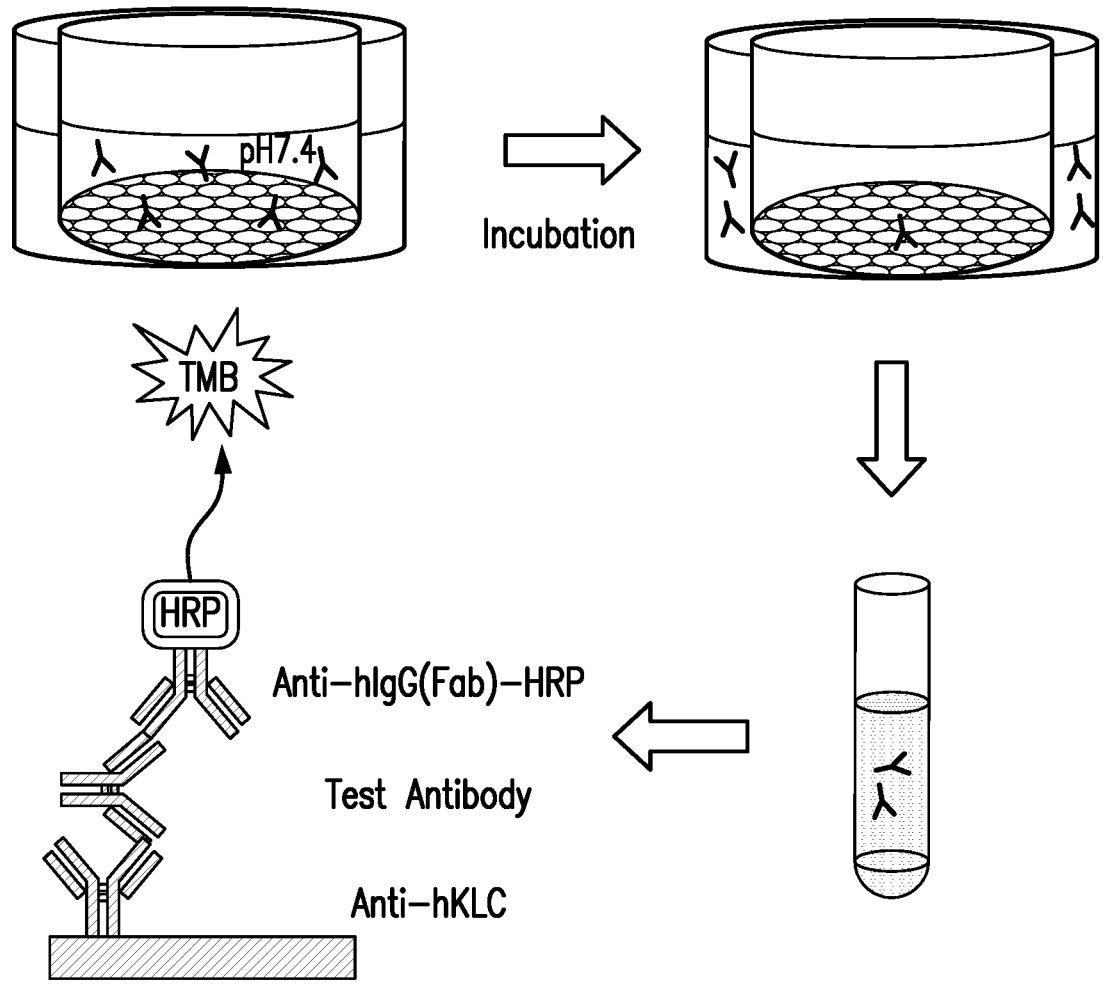
FIG. 1 depicts a schematic of a certain embodiment of transcytosis assays of the present disclosure.

In practicing the presently disclosed subject matter, many conventional techniques in molecular biology, microbiology, cell biology, biochemistry and immunology are used. These techniques are described in greater detail in, for example, Molecular Cloning: a Laboratory Manual 3rd edition, J. F. Sambrook and D. W. Russell, ed. Cold Spring Harbor Laboratory Press 2001; Recombinant Antibodies for Immunotherapy, Melvyn Little, ed. Cambridge University Press 2009; "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction," (Mullis et al., ed., 1994); "A Practical Guide to Molecular Cloning" (Perbal Bernard V., 1988); "Phage Display: A Laboratory Manual" (Barbas et al., 2001). The contents of these references and other references containing standard protocols, widely known to and relied upon by those of skill in the art, including manufacturers' instructions are hereby incorporated by reference as part of the present disclosure.

1. Definitions

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art.

The terms "comprise(s)," "include(s)," "having," "has," "can," "contain(s)," and variants thereof, as used herein, are intended to be open-ended transitional phrases, terms or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

As used herein, the term "about" or "approximately" means within an acceptable error range for the particular value as determined by one of ordinary skill in the art, which will depend in part on how the value is measured or determined, i.e., the limitations of the measurement system. For example, "about" can mean, in certain embodiments, within 3 or more than 3 standard deviations, per the practice in the art. Alternatively, "about" can mean, in certain embodiments, a range of up to 20%, up to 10%, up to 5%, or of up to 1% of a given value. Alternatively, particularly with respect to biological systems or processes, the term can mean within an order of magnitude, e.g., within 5-fold, or within 2-fold, of a value.

As used herein, the terms "medium" and "cell culture medium" refer to a nutrient source used for growing or maintaining cells. As is understood by a person of skill in the art, the nutrient source may contain components required by the cell for growth and/or survival or may contain components that aid in cell growth and/or survival. Vitamins, essential or non-essential amino acids (e.g., cysteine and cystine), and trace elements (e.g., copper) are examples of medium components. Any media provided herein may also be supplemented with any one or more of insulin, plant hydrolysates and animal hydrolysates.

As used herein, the phrase "pharmacokinetic (PK) parameter" refers to any of a variety of PK parameters known in the art, including, but not limited to, clearance (CL), half-life $(t_{1/2})$, area under the curve (AUC), volume of distribution $(V_d)$, and maximum/minimum plasma concentrations $(C_{max}/C_{min})$.

As used herein, the term "clearance" refers to the rate at which a molecule or a polypeptide is removed from the bloodstream.

As used herein, the term "physiological pH" refers to a pH of about 6.5 to about 8.0. n certain embodiments the physiological pH value is any value between about 6.5 and about 8.0, e.g., about 6.6, about 6.7, about 6.8, about 6.9, about 7.0, about 7.1, about 7.2, about 7.3, about 7.4, about 7.5, about 7.6, about 7.7, about 7.8, or about 7.9, or any range within the range of about 6.5 to about 8.0.

"Culturing" a cell refers to contacting a cell with a cell culture medium under conditions suitable to the survival and/or growth and/or proliferation of the cell.

As used herein, a "molecule" refers generally to molecule that is the subject of the assay. For example, but not by way of limitation, the molecule can be any molecule that naturally binds to FcRn or has been engineered to bind to FcRn, such as, but not limited to an albumin-containing molecule, a molecule engineered to bind to FcRn via peptide tags or other amino acid sequences, an antibody, an antibody fragment, or a polyclonal or monoclonal antibody as defined below. Such polypeptides, proteins, antibodies, antibody fragments, or polyclonal or monoclonal antibodies can include non-naturally occurring aspects, including, but not limited to, non-naturally occurring amino acids, non-amino acid linkers or spacers, and can include conjugates to other compositions, e.g., small molecule or large molecule therapeutics.

As used herein, "polypeptide" refers generally to peptides and proteins having more than about ten amino acids. The polypeptides may be homologous to the host cell or may be exogenous, meaning that they are heterologous, i.e., foreign, to the host cell being utilized, such as a human protein produced by a Chinese hamster ovary cell, or a yeast polypeptide produced by a mammalian cell. In certain embodiments, mammalian polypeptides (polypeptides that were originally derived from a mammalian organism) are used and, in certain embodiments, the polypeptides of the present disclosure are directly secreted into the medium.

The term "protein" is meant to refer to a sequence of amino acids for which the chain length is sufficient to produce the higher levels of tertiary and/or quaternary structure. This is to distinguish from "peptides" or other small molecular weight drugs that do not have such structure. Typically, the protein herein will have a molecular weight of at least about 15-20 kD, and in certain embodiments, at least about 20 kD. Examples of proteins encompassed within the definition herein include all mammalian proteins, in particular, therapeutic and diagnostic proteins, such as therapeutic and diagnostic antibodies, and, in general proteins that contain one or more disulfide bonds, including multi-chain polypeptides comprising one or more inter- and/or intrachain disulfide bonds.

The term "antibody" is used herein in the broadest sense and encompasses various antibody structures, including, but not limited to, multispecific antibodies, e.g., bispecific antibodies, and antibody fragments that exhibit the desired antigen-binding activity.

An "antibody fragment," "antigen-binding portion" of an antibody (or simply "antibody portion") or "antigen-binding fragment" of an antibody, as used herein, refers to a molecule other than an intact antibody that comprises a portion of an intact antibody that binds the antigen and/or epitope to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and antibody fragments formed from multispecific, e.g., bispecific antibodies.

The term "monoclonal antibody" or "mAb" as used herein, refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the presently disclosed subject matter may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "hybridoma" refers to a hybrid cell line produced by the fusion of an immortal cell line of immunologic origin and an antibody producing cell. The term encompasses progeny of heterohybrid myeloma fusions, which are the result of a fusion with human cells and a murine myeloma cell line subsequently fused with a plasma cell, commonly known as a trioma cell line. Furthermore, the term is meant to include any immortalized hybrid cell line which produces antibodies such as, for example, quadromas. See, e.g., Milstein et al., Nature, 537:3053 (1983).

As used herein, the term "cell," refers to animal cells, mammalian cells, cultured cells, host cells, recombinant cells, and recombinant host cells. Such cells are generally cell lines obtained or derived from mammalian tissues which are able to grow and survive when placed in media containing appropriate nutrients and/or growth factors.

As used herein, the term "heterologous gene" refers to a gene encoding a protein that is foreign to the host cell being utilized, such as gene encoding a human protein produced by in Chinese hamster ovary cell, or a gene encoding a yeast polypeptide produced in a mammalian cell.

2. Overview

The present disclosure relates to methods and compositions useful for measuring the transcytosis of a molecule of interest. In particular, the present disclosure relates to in vitro receptor-dependent transcytosis assays for evaluating the PK parameters such as clearance rates and/or half-lives of therapeutic antibody molecules. As disclosed in detail herein, the transcytosis of a molecule of interest (e.g., a mAb) measured by the methods of the instant disclosure is highly associated with PK properties of a cell, such as the in vivo clearance of that molecule. Thus, the claimed methods for measuring the transcytosis of a molecule of interest can be used to evaluate the in vivo clearance of the molecule and other PK parameters such as half-life. In certain embodiments, the methods include measuring the transcellular transportation of a plurality of the same molecule of interest from a first chamber to a second chamber, wherein each of the first and second chambers have a physiological pH value (e.g., pH=about 7.4).

Thus, for example, in one aspect, a cell-based assay employing MDCK cells stably expressing human FcRn and B2-microglobulin genes is provided herein to measure transcytosis efficiency of monoclonal antibody (mAb) drugs under conditions relevant to the FcRn-mediated IgG salvage pathway. This transcytosis assay is conducted under physiological pH condition and is designed to assess outcome from combined effects of non-specific binding of IgG to cells, its uptake via pinocytosis, its pH-dependent interactions with FcRn, and dynamics of intracellular trafficking and sorting processes. As described in greater detail in the Examples, the current inventors evaluated 49 mAbs, including 27 marketed mAb drugs, and demonstrated that there was a notable correlation between the clearance rates in human and readouts from assays such as disclosed herein. The expression of FcRn is required to promote the transcytosis of mAbs in the assay and contributes directly to the observed correlation. Further, assays such as provided herein were able to correctly rank order clearance rates of charge or glycosylation variants of Fc-containing molecules in preclinical species. The results provided in the Examples support the utility of the assays disclosed herein as cost effective and animal-saving screening tools for evaluation of mAb-based drug candidates during lead selection and optimization, and process development for desired pharmacokinetic properties.

3. Transcytosis Assay

Transcytosis, which refers to the vesicular transport of macromolecules from one side of a cell to the other, is a strategy used by multicellular organisms to selectively move material between two environments without altering the unique compositions of those environments. Transcytosis is a mechanism for transcellular transport in which a cell encloses extracellular material in an invagination of the cell membrane to form a vesicle, then moves the vesicle across the cell to eject the material through the opposite cell membrane by the reverse process.

In a typical FcRn-mediated transcytosis assay, FcRn-expressing MDCK cells are grown to confluency on filter membranes in trans-well plates, and before the assay, a pH gradient is created by filing the inner chamber with acidic assay buffer (pH<6.0) and the outer chamber with basic assay buffer (pH>7.4). The rationale of this assay design is to take advantage of the pH-dependent binding characteristic of FcRn to facilitate the cellular uptake of test molecules via binding with the FcRn on cell surface under acidic pH and the release of the test molecules under basic pH, both of which improve the robustness and sensitivity of the assay. The current inventors, however, based upon the research described herein, came to recognize that such an assay was inherently flawed for predictive assessment of PK behavior of mAbs. Since the transfected cells typically express high level of FcRn on cell surface and the test antibodies were incubated with the cells in an acidic environment, it was determined that test antibodies exhibiting high binding affinity toward FcRn at acidic pH readily bind to FcRn and enter the cells via FcRn-mediated endocytosis. Yet, the present inventors determined that this is in contrast to what happens in vivo where antibodies bind minimally to cell surface FcRn under physiologic pH, and cellular uptake of mAb is mainly mediated by non-specific fluid-phase pinocytosis. As a consequence, the current inventors determined that the output of the pH gradient transcytosis assay is heavily influenced by the antibody's FcRn binding affinity at acidic pH and therefore unlikely reflects adequately the contribution of other factors that impact PK such as electrostatic interactions and intracellular trafficking parameters. In addition, it was further determined that the artificial pH conditions are intrinsically detrimental to cells which limit the duration of the assay and may potentially create additional assay artifacts.

Accordingly, and as described in greater detail in the Examples, the current inventors developed a different approach to measure transcytosis as a basis for then accurately determining a measure of a PK parameter such as clearance and/or half-life. Thus, for example, in certain embodiments, the present disclosure provides methods for measuring the transcellular transportation of a plurality of a single molecule or a plurality of distinct molecules, comprising: a) introducing the plurality of a single molecule or a plurality of distinct molecules into a first chamber, where the first chamber is separated from a second chamber by a cell or plurality of cells, wherein each of the first and second chambers has a physiological pH value; and b) measuring the number of molecules transcytosed from the first chamber to the second chamber. In certain embodiments, the physiological pH value is about 6.5 to about 8.0. In certain embodiments, the physiological pH value is any value between about 6.5 and about 8.0, e.g., about 6.6, about 6.7, about 6.8, about 6.9, about 7.0, about 7.1, about 7.2, about 7.3, about 7.4, about 7.5, about 7.6, about 7.7, about 7.8, or about 7.9, or any range within the range of about 6.5 to about 8.0. In certain embodiments, the pH of each chamber can differ, as long as both chambers have a physiological pH. For example, but not by way of limitation, the first chamber can have a pH of 6.5 while the second chamber can have a pH of 8.0, or vice versa. In certain embodiments, the physiological pH can be about 7.4.

In certain embodiments, the present disclosure provides methods for determining a pharmacokinetic (PK) parameter of a molecule comprising determining a measure of transcytosis of the molecule or a plurality of the molecules through a cell or a plurality of cells under conditions of physiological pH. In certain embodiments, the PK parameter can be a measure of in vivo clearance of the molecule. In certain embodiments, the PK parameter can be a measure of the in vivo half-life of the molecule. In certain embodiments, the measure of transcytosis can be the rate of transcytosis. In certain embodiments, the measure of transcytosis can be a measure of the amount of the molecule or molecules that is transcytosed. In certain embodiments, the measure of transcytosis can be determined by measuring the transcytosis of the molecule or molecules from a solution in a first chamber to a solution in a second chamber, wherein the first and second chamber are separated by a cell monolayer and the solution in each chamber is at physiological pH. In certain embodiments, the cell or a plurality of cells can be Madin-Darby Canine Kidney (MDCK) cells. In certain embodiments, the cells comprise at least one heterologous gene. In certain embodiments, the at least one heterologous gene can be selected from the group consisting of a FCGRT gene and a B2M gene. In certain embodiments, the cells can express a heterologous cell surface protein. In certain embodiments, the heterologous cell surface protein can comprise a neonatal Fc receptor (FcRn). In certain embodiments, measuring the transcytosis of the molecule can comprise the use of an enzyme-linked immunosorbent assay (ELISA), liquid-scintillation counting (LSC), quantitative PCR, or a fluorescence reader system. In certain embodiments, the methods of the present disclosure can further comprise determining the in vivo clearance of the molecule based on the number of molecules measured. In certain embodiments, the molecule can be a molecule that naturally binds to FcRn or a molecule engineered to bind to FcRn. In certain embodiments, the molecule can be an Fc-containing molecule. In certain embodiments, the molecule can be an antibody. In certain embodiments, the antibody can be a monoclonal antibody. In certain embodiments, the molecule can be an albumin-containing molecule. In certain embodiments, the physiological pH value is about 6.5 to about 8.0. In certain embodiments, the physiological pH value is any value between about 6.5 and about 8.0, e.g., about 6.6, about 6.7, about 6.8, about 6.9, about 7.0, about 7.1, about 7.2, about 7.3, about 7.4, about 7.5, about 7.6, about 7.7, about 7.8, or about 7.9, or any range within the range of about 6.5 to about 8.0. In certain embodiments, the pH of each chamber can differ, as long as both chambers have a physiological pH. For example, but not by way of limitation, the first chamber can have a pH of 6.5 while the second chamber can have a pH of 8.0, or vice versa. In certain embodiments, the physiological pH can be about 7.4.

In certain embodiments, an assay comprises seeding a cell or cells in a cell growth medium onto 96-well Trans-well plates with medium in the inner and outer chambers, removing the medium from the inner chamber, adding the test molecules to the inner chamber, incubating for an amount of time in a tissue culture incubator, collecting the media from the outer chamber and quantifying the test molecules that were transcytosed. In certain embodiments, the cells can be seeded at a density of about $1 \times 10^5$ cells/well in cell growth medium. In certain embodiments, the cell growth medium can be DMEM High Glucose supplemented with 10% FBS, 100 units of Penicillin/Streptomycin, and 5 µg/mL of Puromycin. In certain embodiments, the medium in the inner chamber can be 100 µL and the medium in the outer chamber can be 200 µL. In certain embodiments, the cells can be used on the second day post-plating. In certain embodiments, the test molecules can be added to a final concentration of about 100 µg/mL (0.67 µM) and incubated for 24 hours in a 37° C. tissue culture incubator. In certain embodiments, Lucifer Yellow (Lucifer Yellow CH, dilithium salt; Sigma Aldrich; St. Louis MO) can be prepared in the cell growth medium and can be added to the final 90 minutes of the 24-hour assay incubation. In certain embodiments, the level of passive passage of Lucifer Yellow during the assay can be calculated by dividing the florescent signal in samples from the outer chamber by that of the inner chamber. In certain embodiments, transcytosis results from wells exhibited greater than 0.1% of passive passage of Lucifer Yellow in the outer chamber can be discarded.

In certain embodiments, the test molecule can be added into the outer chamber of a trans-well assay and transcytosis can be detected by measuring the amount of test molecule present in the inner chamber after an appropriate incubation period. In certain embodiments the test molecule is transcytosed from a chamber exposed to the apical membrane of a cell to a chamber exposed to the basolateral membrane of a cell.

In certain embodiments, the present disclosure provides methods for determining or predicting the in vivo clearance of one or more molecules, comprising: a) introducing the molecule(s) into a first chamber of two chambers, where the first chamber is separated from the second chamber by a cell or plurality of cells and wherein each of the first and second chambers has a physiological pH value; and b) measuring the number of molecules transcytosed from the first chamber to the second chamber. In certain embodiments, the physiological pH value is about 6.5 to about 8.0. In certain embodiments, the physiological pH value is any value between about 6.5 and about 8.0, e.g., about 6.6, about 6.7, about 6.8, about 6.9, about 7.0, about 7.1, about 7.2, about 7.3, about 7.4, about 7.5, about 7.6, about 7.7, about 7.8, or about 7.9, or any range within the range of about 6.5 to about 8.0. In certain embodiments, the pH of each chamber can differ, as long as both chambers have a physiological pH. For example, but not by way of limitation, the first chamber can have a pH of 6.5 while the second chamber can have a pH of 8.0, or vice versa. In certain embodiments, the physiological pH can be about 7.4.

In certain embodiments, the present disclosure provides assays for measuring the transcellular transportation of a plurality of the same molecule or a plurality of distinct molecules, comprising a first chamber and a second chamber, each of the first and second chambers having a physiological pH value, wherein the first chamber receives a plurality of the molecules and is configured to allow for transcytosis of the molecules to the second chamber. In certain embodiments, the physiological pH value is about 6.5 to about 8.0. In certain embodiments, the physiological pH value is any value between about 6.5 and about 8.0, e.g., about 6.6, about 6.7, about 6.8, about 6.9, about 7.0, about 7.1, about 7.2, about 7.3, about 7.4, about 7.5, about 7.6, about 7.7, about 7.8, or about 7.9, or any range within the range of about 6.5 to about 8.0. In certain embodiments, the pH of each chamber can differ, as long as both chambers have a physiological pH. For example, but not by way of limitation, the first chamber can have a pH of 6.5 while the second chamber can have a pH of 8.0, or vice versa. In certain embodiments, the physiological pH can be about 7.4.

In certain embodiments, the present disclosure provides assays for determining or predicting the in vivo clearance of one or more molecules, comprising a first chamber and a second chamber, each of the first and second chambers having a physiological pH value, wherein the first chamber receives a plurality of the molecules and is configured to allow for transcytosis of the molecules to the second chamber. In certain embodiments the physiological pH value is about 7.4.

In certain embodiments, the first chamber can comprise a monolayer of cells. In certain embodiments, the cells employed in the assay are selected from the listing provided in Section 3, below. In certain embodiments, the cells employed in the assay are MDCK cells.

In certain embodiments, the cells used in the methods described in the present disclosure can comprise at least one heterologous gene. In certain embodiments, the at least one heterologous gene can be selected from the group consisting of a FCGRT gene and a B2M gene.

In certain embodiments, the cells used in the methods described in the present disclosure can express a cell surface protein. In certain embodiments, the cell surface protein comprises a Fc receptor (FcR). In certain embodiments, the cell surface protein comprises a neonatal Fc receptor (FcRn).

In certain embodiments, the molecules can be labeled or unlabeled. Non-limiting examples of labeled molecules include 3H-labeled, fluorescently labeled molecules, or radioisotopes, e.g., I-125 and P-32.

In certain embodiments, the methods of the present disclosure include measuring the number of the transcellularly transported molecules. In certain, non-limiting embodiments, measuring the number of the transcellularly transported molecules can be performed by enzyme-linked immunosorbent assays (ELISA), liquid-scintillation counting (LSC), quantitative PCR, fluorescence reader systems, confocal microscopy, or live cell imaging systems.

In certain embodiments, the present disclosure provides FcRn-dependent cell-based assays for measuring transcytosis of a mAb, e.g., an IgG mAb, through MDCK cells expressing human FcRn and B2M under conditions resembling the FcRn-mediated IgG salvage pathway. In certain embodiments, the output of this assay involves not only Fc-FcRn interactions at physiological conditions, but also non-specific binding, cellular uptake, sorting and intracellular trafficking processes pertaining to in vivo PK behavior of mAbs.

In certain embodiments, the present disclosure provides methods for correlating transcytosis measured with assays described in the present disclosure with the reported clearance rate in humans of molecules such as polypeptides with diverse structure, function and pharmacological properties.

In certain embodiments, the expression of FcRn may be required to promote the transcytosis of mAbs in the assay and to contribute to the observed association between transcytosis and clearance. In certain embodiments, assays described in the present disclosure are able to rank order clearance rates of charge or glycosylation variants of Fc-containing molecules in preclinical species. In certain embodiments, the assays described in the present disclosure can be used as a time efficient, cost effective and animal saving tool for evaluation of mAb-based drug candidates during lead selection and optimization, and process development for desired pharmacokinetic properties.

In certain embodiments, the present disclosure provides cell-based assays that measure transcytosis efficiency of mAb drugs under physiologically relevant conditions. In certain embodiments, MDCK cells stably expressing human FcRn and B2-microglobulin genes are used in connection with the assays described herein.

In certain embodiments, the present disclosure provides assays that are performed under physiological pH in normal cell culture medium supplemented with fetal bovine serum which supplies bovine albumin that is known to bind to human FcRn (Chaudhury C. et al., 2003, J. Exp. Med. 197, 315-322).

In certain embodiments, the present disclosure provides assays wherein the molecules are taken up by cells via non-specific pinocytosis, interact with human FcRn in the presence of albumin and traverse the cells under conditions relevant to FcRn-mediated mechanism of action.

In certain embodiments, the present disclosure provides assays for determining or predicting clearance of mAbs in human due to the assay's capability of assessing the combined effects of non-specific binding to cells, uptake via pinocytosis, pH-dependent interactions with FcRn, and dynamics of intracellular trafficking and sorting processes.

In certain embodiments, the present disclosure provides assays used to correlate the transcytosis output obtained with the clearance rates of mAbs in humans. In certain embodiments, the output of the assays of the present disclosure can be the concentrations (ng/ml) of a transcytosed molecule in the medium of the outer chamber and the reportable value of the assay can be the average concentration of at least 2 replicate wells from the same plate. In certain embodiments, the output of the assay can be a measure of the rate of transcytosis or a measure of the relative transcytosis of the transcytosed molecule in reference to a control molecule.

In certain embodiments, selection of test molecules of the assays of the present disclosure can be based on availability of the clinical-grade materials and the human clearance data from reliable sources such as, but not limited to, prescribing information, published reports based on population PK models or in-house clinical trials where lineal PK data were generated. In certain embodiments, the usage of clinical-grade materials can ensure that the quality of the test materials can be consistent with those used in clinical studies where the human PK data were generated.

In certain embodiments, assays described in the present disclosure can be used as a tool for in vitro evaluation of potential liabilities in non-specific clearance of drug candidates to support lead selection and optimization, with the aim to rank order candidates and reduce the number of molecules tested in animal models.

In certain embodiments, assays described in the present disclosure can be used to support investigation of mAbs exhibiting undesirable or atypical PK behavior or development of novel mAb drugs with improved transcytosis property pertinent to specialized applications such as crossing of blood-brain barrier for enhanced brain exposure or enhanced disposition in tumor microenvironment for improved tumor targeting.

In certain embodiments, assays described in the present disclosure can be used for the development of improved mechanism-based PK models to support design of optimal dose and dosing schemes in clinical studies.

In certain embodiments, assays described in the present disclosure can be used to demonstrate a correlation between an in vitro readout and in vivo PK data for test molecules.

In certain embodiments, the test molecules can be antibodies. In certain embodiments, the antibodies can be monoclonal or polyclonal antibodies. In certain embodiments, the antibodies may have different structural composition (chimeric, humanized, and fully human). In certain embodiments, the antibodies may consist of varying heavy and light chain sequences (IgG1, IgG2, and IgG4 heavy chains, kappa and lambda light chains). In certain embodiments, the antibodies may recognize different type of targets (membrane bound and soluble). In certain embodiments, the antibodies may exert different therapeutic mechanism of action (agonistic, antagonistic, and cytotoxic). In certain embodiments, the antibodies may and are given to patients via different routes (e.g., iv, im, and sc).

In certain embodiments, the test molecules can be carry engineered mutations that may alter their effector functions (such as but not limited to, atezolizumab, durvalumab), enable association of bi-specific half antibodies (such as, but not limited to, emicizumab), or stabilize IgG4 Fab arms (such as, but not limited to, nivolumab, pembrolizumab).

In certain embodiments, the test molecules can be mAbs exhibiting extreme FcRn binding affinities. In certain embodiments, the observed correlation between transcytosis readout and clearance in human may apply to a broad range of mAbs carrying typical Fc regions. In certain embodiments, the test molecules may be antibodies that are engineered to have altered FcRn binding activity. In certain embodiments, the test molecules may be albumin-containing molecules, or any molecules engineered to bind to FcRn via peptide tags or recombinant proteins. In certain embodiments, the test molecules can be molecules that naturally bind to FcRn. In certain embodiments, the test molecules can be molecules engineered to bind to FcRn.

In certain embodiments, the assays described in the present disclosure may be used to indicate whether or not the expression of human FcRn is required for efficient transcytosis in a transcytosis assay.

In certain embodiments, the assays of the present disclosure may be used to detect and/or indicate that interactions with FcRn contribute to the observed correlation between the transcytosis readout and clearance of the test molecules.

In certain embodiments, the assays of the present disclosure may be used for the binding analysis of the test molecules to a receptor. In certain embodiments, the receptor can be the FcRn receptor. In certain embodiments, the test molecule can be a mAb.

In certain embodiments, assays of the present invention can be used to evaluate the contribution of multiple factors, such as but not limited to, internalization, dynamics of sorting and intracellular trafficking, and exocytosis to the overall efficiency of the recovery process of the test molecule.

In certain embodiments, the assay of the present disclosure can be used to identify and/or detect multiple parameters involved in the FcRn-mediated salvage pathway for determination or prediction of PK of mAbs.

In certain embodiments, the assay of the present disclosure can be used to detect correlation of in vitro transcytosis and in vivo clearance of a molecule. In certain embodiments, the assays of the present disclosure can be used to detect correlation of in vitro transcytosis and in vivo clearance of a molecule as compared to BV ELISA or Fv charge/pI.

In certain embodiments, assays of the present disclosure can be used to evaluate and/or investigate the role of glycosylation on the distribution and catabolism of mAbs in vivo. In certain embodiments, the molecule(s) can be glycoform variants.

In certain embodiments, the assay of the present disclosure can be used to evaluate the role of the addition of sialic acid to the molecule(s) on intracellular trafficking parameters. In certain embodiments, the assay of the present disclosure can be used for the analysis of the involvement of additional mechanisms in clearance of high-mannose and highly sialylated glycoform variants of the molecule(s) in vivo.

In certain embodiments, the assays of the present disclosure can be used as a tool for the study of the FcRn-mediated transcytosis as an elimination mechanism of Abs pertaining to their PK. In certain embodiments, the assays of the present disclosure can be used as a tool for the study and the elucidation of the molecular mechanism governing distribution of FcRn-complexed IgGs.

In certain embodiments, the assays of the present disclosure can provide an output that reflects the target-independent, non-specific clearance mechanism of mAbs with typical FcRn binding affinity in humans.

In certain embodiments, the assays of the present disclosure can be used for the analysis of a diverse group of Fc-containing molecules and respond to factors known to impact PK.

In certain embodiments, the assays of the present embodiment can be used to dissect factors involved in transcytosis assays in order to understand how these factors correlate with in vivo clearance and to define the quantitative nature of this correlation.

In certain embodiments, the assays of the present disclosure can be used for the investigation of the distribution of pinocytosed mAb among recycling, transcytosis, & degradation pathways in various cell type/tissue compartments, as well as the molecular mechanisms governing such distributions in cells involved in the clearance of IgG.

In certain embodiments, the present disclosure is directed to transcytosis assay systems. For example, but not by way of limitation, such systems can comprise: a first chamber and a second chamber, wherein each of the first and second chambers has a physiological pH; a monolayer of cells positioned in the first chamber such that the cells can mediate the transcytosis of a molecule introduced into the first chamber to the second chamber; and a detector for detecting the presence of a molecule in the second chamber. In certain embodiments, the assay systems disclosed herein employ a monolayer of MDCK cells. In certain embodiments, the assay systems disclosed herein employ cells comprising at least one heterologous gene. In certain embodiments, the assay systems disclosed herein employ cells comprising at least one heterologous gene selected from the group consisting of a FCGRT gene and a B2M gene. In certain embodiments, the assay systems disclosed herein employ cells that express a heterologous cell surface protein. In certain embodiments, the assay systems disclosed herein employ cells expressing a heterologous cell surface protein where the heterologous cell surface protein comprises a neonatal Fc receptor (FcRn). In certain embodiments, the assay systems disclosed herein can measure the number of the transcellularly transported molecules via use of an enzyme-linked immunosorbent assay (ELISA), liquid-scintillation counting (LSC), quantitative PCR, or a fluorescence reader system.

4. Cells

Suitable cells to be used in the assays of the present disclosure, include prokaryotic or eukaryotic cells as described herein.

In certain embodiments, vertebrate cells can also be used. Non-limiting examples of useful mammalian cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Additional non-limiting examples of useful mammalian cell lines include Chinese hamster ovary (CHO) cells, including DHFR-CHO cells (Urlaub et al., Proc. Natl. Acad. Sci. USA 77:4216 (1980)) In certain embodiments, the methods of the present disclosure can use hybridoma cells. For example, but not by way of limitation, the hybrid cell line can be of any species, including human and mouse. In certain embodiments, the methods of the present disclosure can use primary and established endothelial and/or epithelial cells. For example, but not by way of limitation, the endothelial and/or epithelial cells can be caco-2, T-84, HMEC-1, MHEC 2.6, HUVEC, and induced pluripotent stem cell (iPSC)-derived cells (Lidington, E. A., D. L. Moyes, et al. (1999). "A comparison of primary endothelial cells and endothelial cell lines for studies of immune interactions." Transpl Immunol 7 (4): 239-246.; Yamaura, Y., B. D. Chapron, et al. (2016). "Functional Comparison of Human Colonic Carcinoma Cell Lines and Primary Small Intestinal Epithelial Cells for Investigations of Intestinal Drug Permeability and First-Pass Metabolism." Drug Metab Dispos 44 (3): 329-335).

In certain embodiments, a cell for use in the disclosed methods can comprise a nucleic acid that encodes a molecule, e.g., a receptor. In certain embodiments, the nucleic acid can be present in one or more vectors, e.g., expression vectors. One type of vector is a "plasmid," which refers to a circular double stranded DNA loop into which additional DNA segments can be ligated. Another type of vector is a viral vector, where additional DNA segments can be ligated into the viral genome. Certain vectors are capable of autonomous replication in a cell into which they are introduced (e.g., bacterial vectors having a bacterial origin of replication and episomal mammalian vectors). Other vectors (e.g., non-episomal mammalian vectors) are integrated into the genome of a cell upon introduction into the cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). Additional non-limiting examples of expression vectors for use in the present disclosure include viral vectors (e.g., replication defective retroviruses, adenoviruses and adeno-associated viruses) that serve equivalent functions.

In certain embodiments, the nucleic acid encoding a molecule, e.g., a receptor, can be introduced into a cell. In certain embodiments, the introduction of a nucleic acid into a cell can be carried out by any method known in the art including, but not limited to, transfection, electroporation, microinjection, infection with a viral or bacteriophage vector containing the nucleic acid sequences, cell fusion, chromosome-mediated gene transfer, microcell-mediated gene transfer, spheroplast fusion, etc. In certain embodiments, the cell is eukaryotic, e.g., a MDCK cell.

5. Trans-Well Assay

Suitable trans-well assays to employs in the methods of the present disclosure include but are not limited to, Boyden chamber assays, cell migration assays, cell invasion assays, microfluidic migration devices, in vitro scratch assays, extracellular matrix (ECM) proteins assays. The methods of the present disclosure can be conducted utilizing a broad variety of assay platforms (e.g., 12-well, 24-well or 96-well multi-well arrays), including "generic" trans-well platforms. Non-limiting examples of assay platforms include MILLI-CELL® cell culture inserts and insert plates, and CORNING® TRANSWELL® polycarbonate membrane cell culture inserts.

EMBODIMENTS OF THE DISCLOSURE

Non-limiting embodiments of the instant disclosure include:
1. A method for determining a pharmacokinetic (PK) parameter of a molecule, the method comprising determining a measure of transcytosis of the molecule or a plurality of the molecules through a cell or a plurality of cells under conditions of physiological pH.
2. The method of embodiment 1, wherein the PK parameter is a measure of in vivo clearance of the molecule.
3. The method of embodiment 1, wherein the PK parameter is a measure of the in vivo half-life of the molecule.
4. The method of any one of embodiments 1-3, wherein the measure of transcytosis is the rate of transcytosis.
5. The method of any one of embodiments 1-3, wherein the measure of transcytosis is a measure of the amount of the molecule or molecules that is transcytosed.
6. The method of embodiment 1, wherein the measure of transcytosis is determined by measuring the transcytosis of the molecule or molecules from a solution in a first chamber to a solution in a second chamber, wherein the first and second chamber are separated by a cell monolayer and the solution in each chamber is at physiological pH.
7. The method of embodiment 1, wherein the cell or a plurality of cells are Madin-Darby Canine Kidney (MDCK) cells.
8. The method of embodiment 1 or 7, wherein the cells comprise at least one heterologous gene.
9. The method of embodiment 8, wherein the at least one heterologous gene is selected from the group consisting of a FCGRT gene and a B2M gene.
10. The method of any one of embodiments 2-9, wherein the cells express a heterologous cell surface protein.
11. The method of embodiment 10, wherein the heterologous cell surface protein comprises a neonatal Fc receptor (FcRn).
12. The method of any one of embodiments 1-11, wherein measuring the transcytosis of the molecule comprises the use of an enzyme-linked immunosorbent assay (ELISA), liquid-scintillation counting (LSC), quantitative PCR, or a fluorescence reader system.
13. The method of any one of embodiments 1-12, further comprising: determining the in vivo clearance of the molecule based on the number of molecules measured.
14. The method of any one of embodiments 1-13, wherein the molecule is a molecule that naturally binds to FcRn.
15. The method of any of embodiments 1-13, wherein the molecule is engineered to bind FcRn.
16. The method of any of embodiments 1-15, wherein the molecule is an Fc-containing molecule.
17. The method of embodiment 16, wherein the Fc-containing molecule is a receptor Fc fusion molecule.
18. The method of any one of embodiments 16, wherein the molecule is an antibody.
19. The method of embodiment 18, wherein the antibody is a monoclonal antibody.
20. The method of any of embodiments 1-19, wherein the molecule is an albumin-containing molecule.
21. The method of any one of embodiments 1-20, wherein the physiological pH value is about 7.4.
22. A method for measuring the transcellular transportation of a plurality of a single molecule or a plurality of distinct molecules, comprising:
    a) introducing the plurality of a single molecule or the plurality of distinct molecules into a first of two chambers where the first chamber is separated from the second chamber by a cell or plurality of cells, and wherein each of the first and second chambers has a physiological pH value; and
    b) measuring the number of molecules transcytosed from the first chamber to the second chamber.
23. The method of embodiment 22, wherein the first chamber comprises a monolayer of cells.
24. The method of embodiment 22 or 23, wherein the cells are Madin-Darby Canine Kidney
(MDCK) cells.
25. The method of embodiment any of embodiments 22 to 24, wherein the cells comprise at least one heterologous gene.
26. The method of embodiment 25, wherein the at least one heterologous gene is selected from the group consisting of a FCGRT gene and a B2M gene.
27. The method of any one of embodiments 22-26, wherein the cells express a heterologous cell surface protein.
28. The method of embodiment 27, wherein the heterologous cell surface protein comprises a neonatal Fc receptor (FcRn).
29. The method of any one of embodiments 22-28, wherein measuring the number of the transcellularly transported molecules comprises the use of an enzyme-linked immunosorbent assay (ELISA), liquid-scintillation counting (LSC), quantitative PCR, or a fluorescence reader system.
30. The method of any of embodiments 22-29, further comprising: determining the in vivo clearance of the molecule based on the number of molecules measured.
31. The method of any one of embodiments 22-30, wherein the molecule is a molecule that naturally binds to FcRn.
32. The method of any of embodiments 22-31, wherein the molecule is engineered to bind FcRn.
33. The method of any of embodiments 22-32, wherein the molecule is an Fc-containing molecule.

34. The method of embodiment 33, wherein the Fc-containing molecule is a receptor Fc fusion molecule.
35. The method of any one of embodiments 22-34, wherein the molecule is an antibody.
36. The method of embodiment 35, wherein the antibody is a monoclonal antibody.
37. The method of any of embodiments 22-36, wherein the molecule is an albumin-containing molecule.
38. The method of any one of embodiments 22-37, wherein the physiological pH value is about 7.4.
39. A method of determining the in vivo clearance of a molecule, comprising:
   a) introducing the molecule into a first of two chambers where the first chamber is separated from the second chamber by a cell or plurality of cells, and wherein each of the first and second chambers has a physiological pH value;
   b) measuring the number of molecules transcytosed from the first chamber to the second chamber; and
   c) determining the in vivo clearance of the molecule based on the number of molecules measured.
40. The method of embodiment 39, wherein the first chamber comprises a monolayer of cells.
41. The method of embodiment 39 or 40, wherein the cells are MDCK cells.
42. The method of any of embodiments 39 to 41, wherein the cells comprise at least one heterologous gene.
43. The method of embodiment 42, wherein the at least one heterologous gene is selected from the group consisting of a FCGRT gene and a B2M gene.
44. The method of any one of embodiments 39 to 43, wherein the cells express a heterologous cell surface protein.
45. The method of embodiment 44, wherein the heterologous cell surface protein comprises a neonatal Fc receptor (FcRn).
46. The method of any one of embodiments 39 to 45, wherein measuring the number of the transcellularly transported molecule comprises the use of an enzyme-linked immunosorbent assay (ELISA), liquid-scintillation counting (LSC), quantitative PCR, or a fluorescence reader system.
47. The method of any one of embodiments 39-46, wherein the molecule is a molecule that naturally binds to FcRn.
48. The method of any of embodiments 39-46, wherein the molecule is engineered to bind FcRn.
49. The method of any of embodiments 39-48, wherein the molecule is an Fc-containing molecule.
50. The method of embodiment 49, wherein the Fc-containing molecule is a receptor Fc fusion molecule.
51. The method of any one of embodiments 39-50, wherein the molecule is an antibody.
52. The method of embodiment 51, wherein the antibody is a monoclonal antibody.
53. The method of any of embodiments 39-52, wherein the molecule is an albumin-containing molecule.
54. The method of any one of embodiments 39-53, wherein the physiological pH value is about 7.4.
55. An assay for measuring the transcellular transportation of a plurality of molecules, comprising a first chamber and a second chamber, each of the first and second chambers having a physiological pH value, wherein the first chamber receives a plurality of molecules, is configured to transcellularly transport the molecules to the second chamber, and the transcellular transportation of the plurality of molecules is measured.
56. The assay of embodiment 55, wherein the first chamber comprises a monolayer of cells.
57. The assay of embodiment 55 or 56, wherein the cells are MDCK cells.
58. The assay of a y of the embodiments 55 to 57, wherein the cells comprise at least one heterologous gene.
59. The assay of embodiment 58, wherein the at least one heterologous gene is selected from the group consisting of a FCGRT gene and a B2M gene.
60. The assay of any one of embodiments 55-59, wherein the cells express a heterologous cell surface protein.
61. The assay of embodiment 60, wherein the heterologous cell surface protein comprises a neonatal Fc receptor (FcRn).
62. The assay of any one of embodiments 55-61, wherein measuring the number of the transcellularly transported molecules comprises use of an enzyme-linked immunosorbent assay (ELISA), liquid-scintillation counting (LSC), quantitative PCR, or a fluorescence reader system.
63. The assay of any one of embodiments 55-62, further comprising: determining the in vivo clearance of the molecules based on the number of molecules measured.
64. The method of any one of embodiments 55-63, wherein the molecule is a molecule that naturally binds to FcRn.
65. The method of any one of embodiments 55-62, wherein the molecule is engineered to bind FcRn.
66. The method of any one of embodiments 55-65, wherein the molecule is an Fc-containing molecule.
67. The method of embodiment 66, wherein the Fc-containing molecule is a receptor Fc fusion molecule.
68. The method of any one of embodiments 55-67, wherein the molecule is an antibody.
69. The method of embodiment 68, wherein the antibody is a monoclonal antibody.
70. The method of any of embodiments 55-69, wherein the molecule is an albumin-containing molecule.
71. The method of any one of embodiments 55-70, wherein the physiological pH value is about 7.4.
72. An assay system comprising:
   a) a first chamber and a second chamber, wherein each of the first and second chambers has a physiological pH;
   b) a monolayer of cells positioned in the first chamber such that the cells can mediate the transcytosis of a molecule introduced into the first chamber to the second chamber; and
   c) a detector for detecting the presence of a molecule in the second chamber.
73. The assay system of embodiment 72, wherein the cells are MDCK cells.
74. The assay system of embodiment 72 or 73, wherein the cells comprise at least one heterologous gene.
75. The assay system of embodiment 74, wherein the at least one heterologous gene is selected from the group consisting of a FCGRT gene and a B2M gene.
76. The assay system of any one of embodiments 72-75, wherein the cells express a heterologous cell surface protein.
77. The assay system of embodiment 76, wherein the heterologous cell surface protein comprises a neonatal Fc receptor (FcRn).

78. The assay system of any one of embodiments 72-77, wherein measuring the number of the transcellularly transported molecules comprises use of an enzyme-linked immunosorbent assay (ELISA), liquid-scintillation counting (LSC), quantitative PCR, or a fluorescence reader system.

EXAMPLES

The following examples are merely illustrative of the presently disclosed subject matter and should not be considered as limitations in any way.

Methods

Test Molecules

Test molecules included 53 mAbs with human clearance data, 5 Fc-fusion proteins, and additional 9 mAbs (4 charge variants, 3 glycosylation variants, and 5 FcRn binding variants). 30 mAbs were marketed therapeutic antibodies of which 19 (Ofatumumab, Vedolizumab, Adalimumab, Natalizumab, Nivolumab, Pembrolizumab, Avelumab, Cetuximab, Palivizumab, Infliximab, Olaratumab, Panitumumab, Resli-zumab, Basiliximab, Ixekizumab, Durvalumab, evo-locumab, alirocumab, golimumab) were purchased from the manufacturers. All the rest were produced in engineered Chinese Hamster Ovary (CHO) cells at Genentech (South San Francisco, CA).

Generation and Characterization of MDCK Cells Expressing Human FcRn and Beta2-Microglubulin Stables cell lines were developed in methods similar to those described previously (Claypool, 2002). Madin-Darby canine kidney II (MDCK II) cells (European Collection of Authenticated Cell Cultures (ECACC), Salisbury, UK) were grown in Dulbecco's modified minimal essential media (DMEM) containing 10% fetal bovine serum (Clontech, Mountain View, CA), 100 units/mL of penicillin, 100 μg/mL streptomycin and 0.292 mg/mL L-Glutamine (Thermo Fisher Scientific, Waltham, MA) in a 37° C., 5% CO2 humidified incubator. Cells were transfected by electroporation (Lonza nucleofector Kit L) with a modified pRK plasmid (Eaton DL et al., 1986, Biochemistry, 25 (26), pp. 8343-8347) containing cDNA for human FcRn (FCGRT (UniProtKB-P55899, FCGRTN_HUMAN) and B2m (UniProtKB-P61769, B2MG_HUMAN)) separated by a P2A sequence (Kim, J H et al., 2011, PLOS One 6 (4): e18556) and under control of a cytomegalovirus (CMV) promoter. After 3 days, the cells were selected with 5 μg/mL of puromycin and expanded for two weeks.

Cells were then sorted for clonality and FCGRT expression by fluorescence-activated cell sorting (FACS) using an anti-FCGRT antibody (ADM31, Aldevron, Fargo, ND) and a secondary anti-mouse PE-conjugated antibody (A10543, Thermo Fisher Scientific, Waltham, MA). All clones were maintained with constant selection agent (5 μg/mL puromycin). The final clone was chosen based on both FCGRT and B2m cell surface expression assessed by Flow cytometry using FITC anti-human B2m FITC-conjugated antibody (2M2, BioLegend, San Diego, CA) using the method described below.

The MDCK-II cells were grown to confluence and detached using a non-enzymatic cell dissociation reagent (SigmaR). $10^6$ cells/ml were first stained with an anti-FCGRT antibody (1:100 dilution) in PBS-0.05M EDTA 2% BSA for one hour on ice. After washing, the cells were incubated with an anti-mouse PE-conjugated secondary antibody (1:200 dilution) and with an anti-β2M FITC-conjugated antibody (1:50 dilution) for one hour on ice, in the dark. The samples were washed and resuspended in PBS-0.05M EDTA 2% BSA for flow cytometry analysis on a BD FACSCanto II (BD Biosciences, San Jose, CA).

Transcytosis Assay

Cells were seeded at a density of $1\times10^5$ cells/well in cell growth medium DMEM High Glucose supplemented with 10% FBS, 100 units of Penicillin/Streptomycin, and 5 μg/mL of Puromycin onto 96-well Trans-well" plates (Corning® Costar, Acton, MA, USA), with 100 and 200 μL of medium in the inner and outer chambers, respectively. Cells were used for experiments on the second day post-plating. The medium in the inner chamber was removed and test molecules were added to a final concentration of 100 μg/mL (0.67 μM) and incubated for 24 hours in a 37° C. tissue culture incubator. Luciferin Yellow (Lucifer Yellow CH, dilithium salt; Sigma Aldrich "; St. Louis MO) prepared in the cell growth medium was added to the final 90 minutes of the 24-hour assay incubation. Media from the outer chamber were collected and amount of transcytosed molecules were quantified (FIG. 1). The level of passive passage of Lucifer Yellow during the assay was calculated by dividing the florescent signal in samples from the outer chamber by that of the inner chamber. Transcytosis results from wells exhibited greater than 0.1% of passive passage of Lucifer Yellow in the outer chamber were discarded.

The output of the assay was the concentrations (ng/ml) of a transcytosed molecule in the medium of the outer chamber and the reportable value of the assay is the average concentration of 2 replicate wells from the same plate. In certain embodiments, the output of the assay can be a measure of the rate of transcytosis or a measure of the relative transcytosis of the transcytosed molecule.

Quantification of Transcytosis 96-well microtiter plates were coated with 100 μL of goat anti-human IgG-F(ab)' (Jackson ImmunoResearch Laboratories, West Grove, PA) at 1 μg/mL in sodium carbonate (pH 9.6) at 2-8° C. overnight. After washing with PBS/0.05% polysorbate-20, plates were incubated with 200 μL of a blocking buffer (PBS/0.5%; BSA/0.1%; casein/0.05%; P20/0.05%; Proclin300) at room temperature for 2 hours with gentle agitation. After washing, 100 μL of serially diluted assay standards, controls, or samples in assay diluent (PBS/0.5%; BSA/0.05%; P20/0.05%; Proclin300) were added to the plate (FIG. 1). After incubating at room temperature for another hour with gentle agitation, the plate was washed again before incubating with 100 μL of the goat anti-human IgG-Fc conjugated to HRP (Jackson ImmunoResearch Laboratories, West Grove, PA) at a 1:10000 dilution in assay diluent. The plate was incubated for 1 hour with gentle agitation and after wash, 100 μL of freshly mixed 3,3',5,5'-Tetramethylbenzidine (TMB) solution (Kirkegaard & Perry Laboratories, Gaithersburg, MD) was added. Color was allowed to develop for 15 min without agitation, and the reaction was stopped by the addition of 100 μL of 1 M $H_3PO_4$. The absorbance was read at a wavelength of 450 nm with 650 nm reference on a Spectra Max 13 plate reader (Molecular Devices Corporation, CA), and the data were processed using the SoftmaxPro® software provided by the manufacturer. Concentrations of test antibodies in samples were interpolated from a four-parameter fit of the standard curve on the same plate.

For Fc-fusion proteins, the test molecules were captured by antibodies bind specifically to the protein and detected by anti-human IgG-F(ab)' conjugated to HRP following the procedures described above.

BV ELISA

A 1% baculovirus particle suspension was prepared in coating buffer (0.05 Sodium Carbonate pH 9.6) and 25 μL were added per well in a 384-well plate (Nunc-Immuno Plate MaxiSorp Surface, Cat. #464718) and incubated overnight at 4° C. Wells were blocked with 50 µL of assay buffer (PBS containing 5% BSA and 10 PPM Proclin) for 1 h at room temperature with gentle shaking. After washing the wells three times with 100 µl washing buffer (PBS), 25 µL of samples prepared in assay buffer were loaded in duplicate and incubated for 1 h at room temperature with gentle shaking. Plates were washed six times with 100 µl washing buffer and 25 µl of goat anti-human FcRn fragment specific conjugated to horseradish peroxidase (Jackson ImmunoResearch) at 10 ng/mL in assay buffer was added to each well and incubated for 1 h at room temperature with gentle shaking. Wells were washed six times with 100 µL washing buffer, 25 µL of TMB (Moss, Inc., Cat. #TMBE-1000) substrate was added per well for 15 min at room temperature with gentle shaking, 25 µL of 1M phosphoric acid was added per well to stop the reaction, and absorbance at 450 nm was measured using a plate reader.

BLI-Based Assessment of mAb-FcRn Interactions

The Octet RED (PALL/ForteBio) was used for all FcRn binding in vitro assays at 30° C. in 96-well solid black plates (Greiner Bio-One, 655900). Initially, FcRn was immobilized to nickel-nitrilotriacetic acid-coated biosensors (ForteBio, 18-0029) for 180 seconds at an optimized concentration. After a baseline step, the mAb-FcRn binding rate was determined when the biosensor with immobilized FcRn was exposed to the mAb sample in PBS adjusted to pH 6.0 with HCl for 30 seconds. Prior to analysis, all antibodies were dialyzed into PBS pH 6.0, diluted to 100 mg/mL in PBS pH 6.0 and used at a 200 mL volume. Each assay is performed on a specific mAb in quintuplicate. Data analysis was performed using software version 7.0 (PALL, ForteBio).

pI Determination by Imaged Capillary Isoelectric Focusing

Imaged capillary isoelectric focusing (icIEF) was performed on an iCE280 Analyzer (ProteinSimple, Toronto, ON) as described previously (Li et al, 2014). The anolyte and catholyte were 80 mM phosphoric acid and 100 mM NaOH, respectively, each prepared with 0.1% methylcellulose. mAb samples were prepared in water containing carboxypeptidase and incubated at 37° C. for 20 min to remove C-terminal lysine residues. Ampholyte mixture comprised of 3.1% (v/v) Pharmalytes (GE Life Sciences), 2.5 M urea, 0.1% (v/v) methylcellulose, and pI 5.5 and 9.77 markers (Protein Simple) was combined with treated antibody to a final concentration of 0.25 mg/mL. Electropherograms were imaged with the optical absorption detector at 280 nm.

Cell Binding Assay by Flow Cytometry

The cells were stained with test molecules at 100 g/mL in FACS buffer (PBS/1% BSA/2 mM EDTA/0.1% sodium azide) and incubated for one hour on ice. After washing with FACS buffer, cells were stained with PE conjugated mouse anti human IgG Fc secondary antibody (Southern Biotech, Birmingham, AL) for 1 hour on ice. Cells were washed and fixed with fixation buffer (BD Biosciences, San Jose, CA). The fluorescence intensity of stained cells was measured using a FACSCanto II flow cytometer (BD Biosciences; San Jose, CA) and the data analyzed using FlowJo software (Tree Star; Ashland, OR).

Mouse PK study with X-Fc Sialylation Variants

A single I. V bolus dose of X-Fc variants (1, 5, 8, 12 or 15) were administered to CD1 mice at 1 mg/kg dose. At various timepoints up to 21 days post-dose, serum samples (n=4/timepoint) were collected and analyzed for drug concentrations. Drug concentrations in serum were measured using a validated ELISA assay. Serum concentration-time data from individual animals were used to estimate pharmacokinetic parameters using a non-compartmental sparse analysis in Phoenix WinNonlin™, Version 6.4.0.768 (WinNonlin 6.4; Pharsight Corporation, Mountain View, CA).

Total antibody concentrations in mouse serum were measured with an ELISA using the Gyros technology platform (Gyros US Inc., Warren, NJ) and a generic PK assay. This assay uses biotinylated sheep anti-human IgG antibody as capture and Alexa Fluor_647-conjugated sheep anti-human IgG as detection. The minimum dilution for this assay was 1:10. The assay has a standard curve range of 0.03-30 µg/mL for mouse serum.

Figures 2A, 2B:
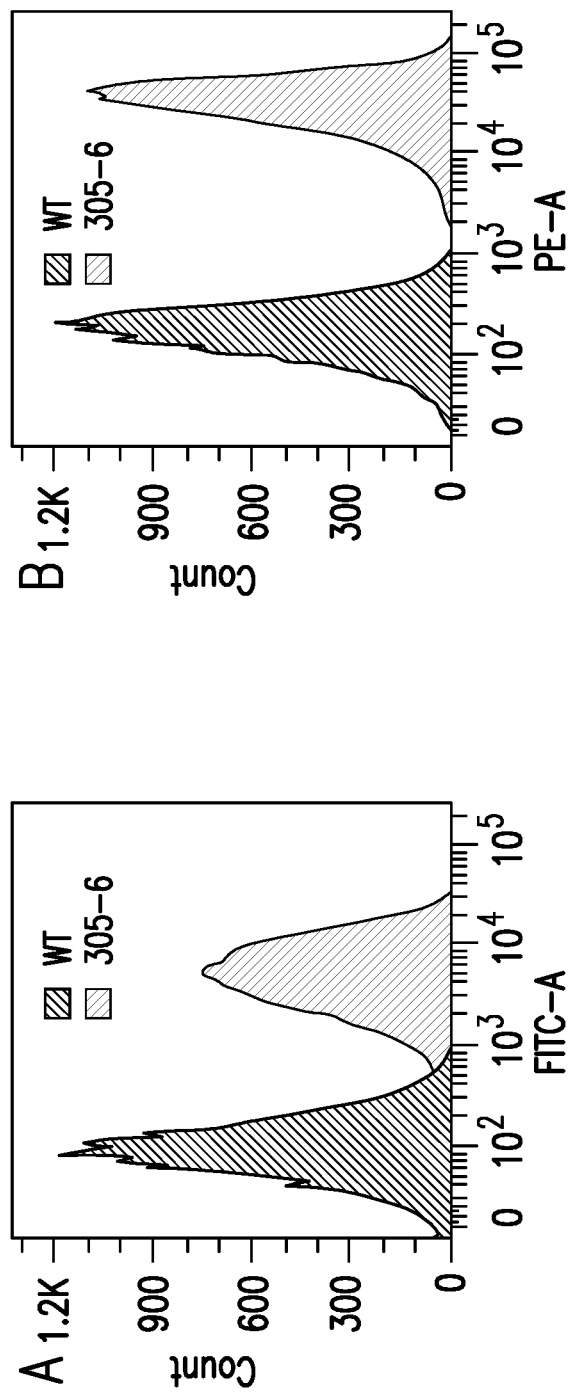
FIGS. 2A-2B depict the expression of human FcRn heavy chain and beta2-microglobulin on transfected clonal MDCK cell line 305-6.

Example 1: Development and Characterization of a Neutral pH FcRn-Mediated Transcytosis Assay MDCK cell lines were transfected with both human B2M (B2M) and FcRn heavy chain (FCGRT) genes. Stable cells expressing both genes were isolated by FACS sorting and a clonal cell line (MDCK-hFcRn; 305-6) expressing high levels of FCGRT and B2M on cell surface (FIG. 2) was selected for further development of a FcRn-dependent transcytosis assay. To minimize potential assay bias/artifacts and to better mimic physiological conditions, molecules tested in the assay were free of label and the assay was conducted in growth medium under physiological pH.

In the present assay, cells were grown to confluency on filter membrane of trans-wells, test molecules were added to the growth medium in the inner chamber, and after incubation, the molecules transported through cells and released into the medium in the outer chamber were quantified by ELISA. The assay was extensively optimized for seeding density, trans-well plate format, loading concentration, assay medium, and assay duration Since the assay medium contains bovine serum albumin (BSA) which has been shown to bind to human FcRn and form a tri-molecule complex in the presence of IgG (Chaudhury C. et al., 2003, J. Exp. Med. 197, 315-322), the human FcRn in this assay is expected to engage both the test antibodies and BSA at the same time. Alternative assay media containing varying amount of human serum albumin instead of BSA showed little differences in transcytosis readout compared to the medium containing BSA. Due to operational considerations, the assay was conducted in normal growth medium containing FBS/BSA.

The functional integrity of filter-grown MDCK-hFcRn cells was monitored by measurements of the trans-epithelial electrical resistance (TEER; Srinivasan B. et al., 2015, J Lab Autom 20 (2): 107-126). The TEER of monolayers before the assay typically ranged from 250-300 $\Omega*cm^2$, a characteristic range for polarized MDCK II cells (Tesar D B et al., 2006, Traffic 7 (9): 1127-1142). In addition, the barrier integrity (leakiness) of the monolayer during the assay was monitored by spiking Lucifer Yellow along with the test molecules in the inner chamber as described in the Methods.

Example 2: Correlation of In Vitro Transcytosis Efficiency with In Vivo Clearance of mAbs in Humans To evaluate potential utility of this assay for determination or prediction of PK behavior of mAbs in vivo, 53 mAbs, including 30 marketed therapeutic antibodies and 23 clinical candidates, were tested in the assay. The transcytosis outputs of the mAbs were analyzed for potential correlations with their reported clearance rates in human. These molecules were selected based on availability of clinical-grade material as well as human clearance data. In addition to the transcytosis assay, some of the molecules were also tested in two other in vitro assays: BV ELISA, and biolayer interferometry (BLI)-based human FcRn binding assay. The BV ELISA measures non-specific binding to baculovirus particles as an indication of general non-specific binding property of mAbs and has been reported to be able to identify antibodies having increased risk for fast clearance in cynomolgus monkeys (Hötzel, et al., 2012, (2012), MAbs 4 (6): 753-760). The BLI-based FcRn binding assay has been used to generate combined FcRn association rates at pH 6.0 and dissociation rates at pH 7.4 which showed a strong correlation with half-lives of five mAbs in human and mice transgenic for human FcRn (Souders CA et al., 2015, MAbs 7 (5): 912-921).

Results of this study are presented in Table 1 that also include test molecule's clearance rate in both human and cynomolgus monkey (cyno). The mean transcytosis output of the test panel is 5.4 ng/mL with a medium of 4.5 and a range of 2.6-14.9, which reflects an average of about 0.005% of the materials loaded in the inner chamber (100 μg/mL). The respective mean and medium/range of FcRn binding affinity at pH 6.0 (Kd in μM) and BV ELISA score are as follows: 0.63, 0.54/0.25-1.8; and 0.25, 0.06/0.0.038-3.916 respectively. The human clearance rates of marketed mAb drugs were obtained from the drug's prescribing information or published reports; the clearance rates of clinical stage mAbs were generated from clinical studies conducted by Genentech or published reports. The cyno clearance rates were generated from cyno studies conducted by Genentech. The mean and medium/range of clearance rate in human are 5.0, 4.1/1.4-14.1 mL/Kg/Day, and 6.8, 4.9/3.0-15.8 mL/Kg/Day in cyno. It appears that the values of all the parameters spread over at least a 5-fold range indicating substantial diversity of the mAbs panel tested in this study.

Figures 3A, 3B, 3C, 3D, 3E:
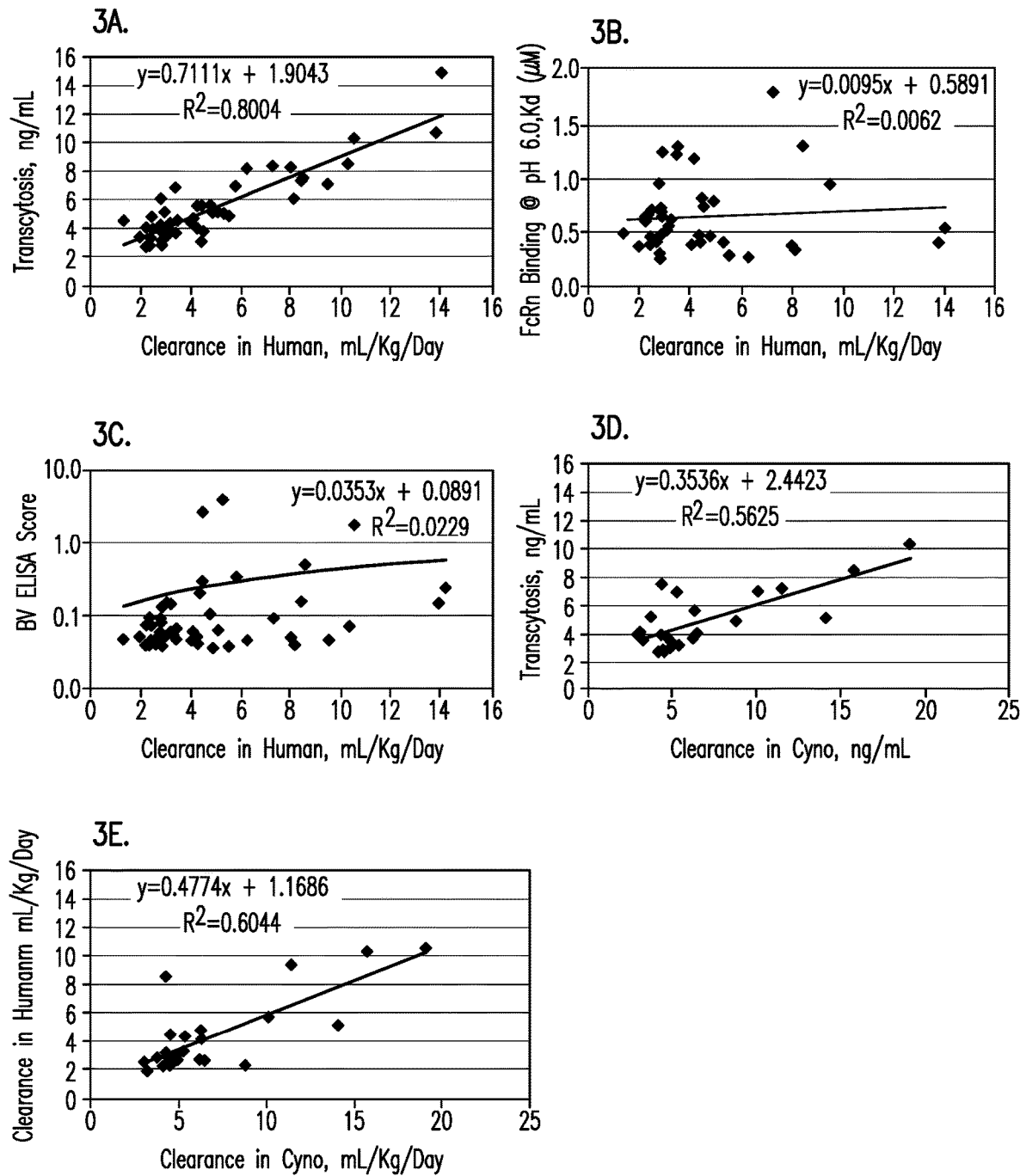
FIGS. 3A-3E show scatter plots depicting relationships between clearance in human (rate in mK/Kg/Day) and either transcytosis value (FIG. 3A; concentration in ng/mL), FcRn binding affinity at pH6.0 (FIG. 3B; Kd in M), or BV ELISA score (FIG. 3C). In addition, clearance rates of mAbs in cynomolgus monkey (rate in mK/Kg/Day) were plotted against either the transcytosis values (FIG. 3D) or clearance rates in human (FIG. 3E). Data were fitted with a linear regressing model and both the equation and the R-squared value are presented.

As shown in FIG. 3A, an apparent trend of association was observed between the transcytosis outputs and clearance values with a fitted linear regression R-squared value of 0.8. Antibodies with reported faster clearance rates in human in general showed higher transcytosis outputs in this assay. Of note, the observed correlation was not affected by sub-grouping test molecules based on heavy and light chain subclass, target nature (soluble or membrane-bound), mechanism of action (agonistic, antagonistic, or cytotoxic) or route of administration. On the other hand, clearance rates showed no apparent correlation with FcRn binding at pH 6.0 via BLI or BV ELISA (FIG. 3B, C).

Cyno PK in general provides the most translatable model for determining or predicting human PK of mAbs. A correlation between transcytosis output and cyno clearance may provide additional confirmation for the utility of this assay as a determinative or predictive tool for PK. Cyno clearance data were obtained for 25 mAbs in the panel and their correlation with either human clearance rates or the transcytosis efficiency values were analyzed. As shown in Figure D, a trend of association was observed between transcytosis efficiency and cyno clearance, and the extent of correlation as judged by R-squared value appeared similar to that between cyno and human clearance (FIG. 3D). However, at around 0.6, R-squared values were relatively low due to a few "outliers". Two of the most obvious outliers in the cyno clearance vs transcytosis plot (FIG. 3D) were aNRP1 and pertuzumab; the former is known for its discordance with human clearance (FIG. 3E), the later binds to MDCK cells presumably due to cross reactivity with canine epidermal growth factor receptor-2 (Fazekas, 2016). Removal of these two molecules increased the R-squared value of the lineal regression fit to about 0.75 in FIG. 2E and 0.76 in FIG. 3E.

TABLE 1

| No. | mAb ID | Isotype | Clearance in Human, mL/Day/Kg | Clearance in Cyno, mL/Day/Kg | Transcytosis, ng/mL | FcRn Binding, pH 6.0, $K_D$ (μM) | BV ELISA, Score | Target | ROA |
|---|---|---|---|---|---|---|---|---|---|
| 1 | Trastuzumab | IgG1/Kappa | 2.9 | 4.4 | 2.7 | 0.68 | 0.038 | M | iv |
| 2 | Omalizumab | IgG1/Kappa | 2.4 | 4.5 | 2.7 | 0.37 | 0.041 | S | sc |
| 3 | Rituximab | IgG1/Kappa | 4.8 | 6.3 | 5.6 | 0.46 | 0.103 | M | iv |
| 4 | Ocrelizumab | IgG1/Kappa | 2.4 | 8.7 | 4.8 | 0.45 | 0.045 | M | iv |
| 5 | Pertuzumab | IgG1/Kappa | 3.4 | 5.2 | 6.8 | 0.57 | 0.047 | M | iv |
| 6 | Bevacizumab | IgG1/Kappa | 3.1 | 4.8 | 3.4 | 0.56 | 0.150 | S | iv |
| 7 | Atezolizumab | IgG1/Kappa | 2.9 | 4.9 | 3.0 | 0.65 | 0.050 | M | iv |
| 8 | Tocilizumab | IgG1/Kappa | 4.3 | 6.3 | 5.5 | 0.46 | 0.049 | M | sc |
| 9 | Efalizumab | IgG1/Kappa | 7.3 | NA | 8.3 | 1.80 | 0.091 | M | sc |
| 10 | Ofatumumab | IgG1Kappa | 3.2 | NA | 4.3 | 0.55 | 0.059 | M | iv |
| 11 | Vedolizumab | IgG1/Kappa | 2.2 | NA | 4.1 | 0.61 | 0.071 | M | iv |
| 12 | Adalimumab | IgG1/Kappa | 4.1 | NA | 4.7 | 1.18 | 0.058 | S | sc |
| 13 | Natalizumab | IgG4/Kappa | 5.5 | NA | 4.9 | 0.28 | 0.037 | M | iv |
| 14 | Nivolumab | IgG4/Kappa | 2.8 | NA | 4.3 | 0.25 | 0.053 | M | iv |
| 15 | Pembrolizumab | IgG4/Kappa | 2.8 | NA | 4.2 | 0.29 | 0.085 | M | iv |
| 16 | Avelumab | IgG1/Lambda | 8.4 | NA | 7.3 | 1.30 | 0.155 | M | iv |
| 17 | Cetuximab | IgG1/Kappa | 8.1 | NA | 6.1 | 0.34 | 0.039 | M | iv |
| 18 | Palivizumab | IgG1/Kappa | 2.8 | NA | 3.8 | 0.48 | 0.075 | S | im |
| 19 | Infliximab | IgG1/Kappa | 4.5 | NA | 5.6 | 0.80 | 2.683 | S | iv |
| 20 | Olaratumab | IgG1/Kappa | 8.0 | NA | 8.2 | 0.38 | 0.049 | M | iv |
| 21 | Panitumumab | IgG2/Kappa | 4.9 | NA | 5.0 | 0.78 | 0.037 | M | iv |
| 22 | Reslizumab | IgG4/Kappa | 2.4 | NA | 3.3 | 0.45 | 0.088 | S | iv |
| 23 | Basiliximab | IgG1/Kappa | 14.1 | NA | 14.9 | 0.54 | 0.234 | M | iv |
| 24 | Ixekizumab | IgG4/Kappa | 5.1 | NA | 5.1 | ND | 0.061 | S | sc |
| 25 | Durvalumab | IgG1/Kappa | 2.8 | NA | 6.0 | 0.70 | 0.058 | M | iv |
| 26 | Obinutuzumab | IgG1/Kappa | 1.4 | NA | 4.5 | 0.49 | 0.046 | M | iv |
| 27 | Emicizumab | IgG1/Kappa | 3.4 | NA | 3.6 | 1.23 | 0.050 | S | sc |
| 28 | Evolocumab | IgG2/Kappa | 4.1 | NA | 3.6 | ND | ND | S | sc |
| 29 | Alirocumab | IgG1/Kappa | 11.4 | NA | 9.9 | ND | ND | S | sc |
| 30 | Golimumab | IgG1/Kappa | 7.5 | NA | 6.8 | ND | ND | S | sc |
| 31 | mAb 1 | IgG1/Kappa | 3.5 | NA | 4.5 | 1.29 | 0.066 | M | sc |
| 32 | mAb 2 | IgG4/Kappa | 2.8 | 6.4 | 4.0 | 0.95 | 0.053 | S | iv |

TABLE 1-continued

| No. | mAb ID | Isotype | Clearance in Human, mL/Day/Kg | Clearance in Cyno, mL/Day/Kg | Transcytosis, ng/mL | FcRn Binding, pH 6.0, $K_D$ (μM) | BV ELISA, Score | Target | ROA |
|---|---|---|---|---|---|---|---|---|---|
| 33 | mAb 3 | IgG1/Lambda | 4.4 | 5.4 | 3.1 | 0.40 | 0.207 | M | iv |
| 34 | mAb 4 | IgG1/Kappa | 6.3 | NA | 8.2 | 0.26 | 0.046 | M | iv |
| 35 | mAb 5 | IgG1/Kappa | 2.0 | 3.3 | 3.3 | 0.37 | 0.051 | M | sc |
| 36 | mAb 6 | IgG1/Kappa | 8.5 | 4.3 | 7.4 | ND | 0.480 | M | iv |
| 37 | mAb 7 | IgG1/Kappa | 9.5 | 11.5 | 7.1 | 0.94 | 0.045 | S | sc |
| 38 | mAb 8 | IgG1/Kappa | 5.8 | 10.1 | 6.9 | ND | 0.341 | M | sc |
| 39 | mAb 9 | IgG1/Kappa | 3.2 | 4.3 | 3.9 | 0.61 | 0.146 | S | iv |
| 40 | mAb 10 | IgG1/Kappa | 5.3 | 14.1 | 5.0 | 0.40 | 3.916 | M | iv |
| 41 | mAb 11 | IgG4/Kappa | 2.2 | 4.1 | 2.6 | 0.65 | 0.038 | S | sc |
| 42 | mAb 12 | IgG1/Lambda | 10.6 | 19.1 | 10.2 | ND | 1.745 | S | sc |
| 43 | mAb 13 | IgG1/Kappa | 4.3 | NA | 3.9 | 0.42 | 0.042 | M | iv |
| 44 | mAb 14 | IgG2/Kappa | 2.4 | NA | 4.0 | 0.70 | 0.075 | M | sc |
| 45 | mAb 15 | IgG1/Kappa | 4.0 | NA | 4.4 | 0.38 | 0.045 | M | iv |
| 46 | mAb 16 | IgG1/Kappa | 2.9 | 6.2 | 3.6 | 1.24 | 0.134 | S | sc |
| 47 | mAb 17 | IgG1/Kappa | 4.5 | 4.6 | 3.8 | 0.73 | 0.296 | M | iv |
| 48 | mAb 18 | IgG1/Lambda | 2.7 | 3.0 | 3.9 | 0.44 | 0.041 | S | iv |
| 49 | mAb 19 | IgG1/Kappa | 3.0 | 3.8 | 5.1 | 0.48 | 0.048 | S | iv |
| 50 | mAb 20 | IgG1/Kappa | 2.7 | 3.1 | 4.0 | 0.40 | 0.051 | S | sc |
| 51 | mAb 21 | IgG1/Kappa | 10.3 | 15.8 | 8.4 | ND | 0.071 | M | iv |
| 52 | mAb 22 | IgG1/Kappa | 13.8 | NA | 10.6 | 0.41 | 0.147 | M | iv |
| 53 | mAb 23 | IgG1/Kappa | 7.2 | 4.8 | 6.2 | 0.75 | 0.044 | S | sc |
| Mean | | | 5.0 | 6.8 | 5.4 | 0.63 | 0.25 | | |
| SD | | | 3.0 | 4.2 | 2.4 | 0.33 | 0.69 | | |
| Medium | | | 4.1 | 4.9 | 4.7 | 0.54 | 0.06 | | |
| Range | | | 1.4-14.1 | 3.0-15.8 | 2.6-14.9 | 0.25-1.8 | 0.038-3.916 | | |

ND = Not Done; NA = Not Available; ROA = Route of administration; M = membrane-bound; S = Soluble; SC = subcutaneous injection; IV = intravenous injection; IM = intramucular injection.

Figures 4A, 4B, 4C:
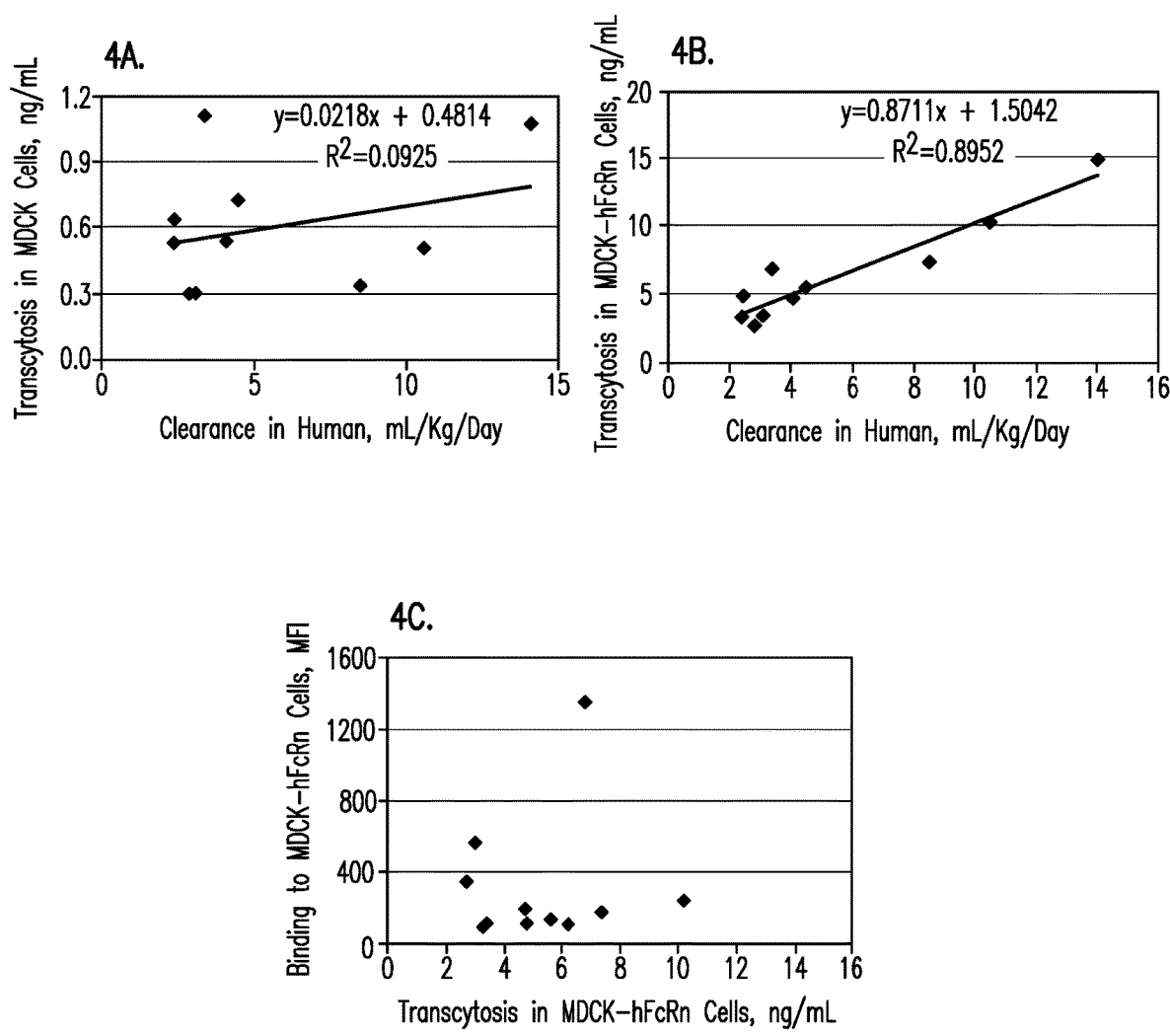
FIGS. 4A-4C show the relationships between clearance in human and either transcytosis in MDCK cells (FIG. 4A) or MDCK-hFcRn cells (FIG. 4B), as well as binding to MDCK-hFcRn cells and transcytosis in MDCK-hFcRn cells (FIG. 4C).

To demonstrate the dependence on FcRn interactions in the observed correlation between the transcytosis output and clearance, 12 mAbs (10 from the panel with human clearance data) were randomly selected based on their varying transcytosis outputs observed in the assay and tested in a similar transcytosis assay using the parent MDCK cells. The resulting transcytosis values were analyzed for trend of correlation with their clearance rate (FIG. 4A) and compared to those using the MDCK-hFcRn cells (FIG. 4B). As shown in Table 3 and FIG. 4A, transcytosis values in MDCK cells were in general less than 10% of those from assays using the FcRn-transfected cells, and showed no apparent correlation with clearance rates in human. On the other hand, transcytosis in MDCK-hFcRn cells with the same set of mAbs show a strong correlation with clearance (FIG. 4B). Results of this study support that interactions between FcRn and test antibodies are not only involved in promoting the transcytosis in the present assay but also contributed directly to their observed correlation with clearance in humans.

Example 3: Impact of Cell Binding on Transcytosis of mAbs

Non-specific off-target binding is known to impact PK of mAb drugs (Boswell et al., 2010, Bioconjug. Chem. 21, 2153-2163). Transcytosis of test molecules in the present assay involved binding and internalization by MDCK-hFcRn cells. Test molecules may bind to the cells via non-specific interactions or specific binding to cell surface FcRn at physiological pH, both of which may impact the transcytosis outputs. To evaluate impact of cell binding on transcytosis, selective mAbs were incubated with both the transfected MDCK-hFcRn and the non-transfected MDCK cells, and the bound antibodies were detected with a fluorescent-conjugated mouse anti-human IgG-Fc by flow cytometry. The degrees of binding to cells were indicated by geometric mean florescence intensity and the results are presented in Table 2. It appeared that with a few exceptions, differences among the mAbs in cell binding to either cell line were mostly small, which indicate that due to the minimal binding to FcRn at physiological pH, FcRn expression in most cases didn't change the binding behavior of Abs to MDCK cells dramatically. No apparent correlations were observed between cell binding and the transcytosis output (FIG. 4C).

Interestingly, both anti-HER2 antibodies, trastuzumab and pertuzumab, showed elevated binding to MDCK cells with and without the transfected human FcRn (Table 2). It has been reported that human HER2 share high homology to its canine counterpart and that both trastuzumab and pertuzumab may be used for treatment of mammary carcinomas in dogs (Fazekas, 2016). Therefore, the observed binding to cells by these two molecules can be explained by cross-reactivity to canine epidermal growth factor receptor-2 expressed on MDCK cells. In addition, anti-gD showed increased binding to MDCK-hFcRn but not to non-transfected MDCK cells suggesting its specific binding to human FcRn on MDCK-FcRn cells at physiological pH. Further, the elevated binding to MDCK-FcRn cells did not translate to increased transcytosis in MDCK-FcRn cells. It is possible that the observed binding did not directly lead to internalization of the complex; alternatively, the internalized anti-gD was preferentially recycled back to inner chamber or directed to lysosome for degradation, therefore was not transported via the transcytosis pathway. Lastly, two of the mAbs (baxiliximab and mAb 12) exhibiting higher transcytosis and faster clearance among the 12 mAbs tested, also showed elevated binding to both cell lines. It suggests both molecules may exert non-specific interactions with MDCK cell membrane which led to increased transcytosis in the assay and potentially played a role in their reported fast clearance in humans.

TABLE 2

| mAb ID | Transcytosis in MDCK cells, ng/mL | Transcytosis in MDCK-hFcRn cells, ng/mL | Clearance Rate in Humans, mL/Kg/Day | Binding to MDCK cells, MFI | Binding to MDCK-FcRn cells, MFI |
|---|---|---|---|---|---|
| Bevacizumab | 0.3 | 3.4 | 3.1 | 81 | 102 |
| Trastuzumab | 0.3 | 2.7 | 2.9 | 178 | 336 |
| Pertuzumab | 1.1 | 6.8 | 3.4 | 1005 | 1354 |
| Ocrelizumab | 0.5 | 4.8 | 2.4 | 78 | 101 |
| Basiliximab | 1.1 | 14.8 | 14.1 | 111 | 203 |
| Infliximab | 0.7 | 5.6 | 4.5 | 99 | 128 |
| Adalimumab | 0.5 | 4.7 | 4.1 | 77 | 183 |
| Reslizumab | 0.6 | 3.3 | 2.4 | 74 | 93 |
| mAb 6 | 0.3 | 7.4 | 8.5 | 111 | 168 |
| mAb 12 | 0.5 | 10.2 | 10.6 | 103 | 233 |
| mAb 23 | 0.8 | 6.2 | 7.2 | 75 | 98 |
| mAb 24 | 0.3 | 3.0 | NA | 79 | 561 |
| No mAb | NA | NA | NA | 75 | 94 |

Taken together, results from this study suggest that whereas binding to cells via specific or non-specific interactions may impact transcytosis, the output from this assay is not determined by binding only; other contributing factors such as cellular uptake/internalization, interaction with FcRn in endosome, and sorting/trafficking in the cells were involved for the integrated outcome. MFI: geometric mean fluorescence intensity.

Example 4: Impact of Charge on Transcytosis of mAbs

Charge is one of the major determinants of how a mAb interacts with the negatively charged components on the cell surface. Changes in charge have been shown to change the PK behavior of mAbs: mAbs carrying higher pI or more positive Fv charge were shown to be cleared faster than their lower pI/less positive charged counterparts (Igawa, T. et al., 2010, Protein Eng Des Sel 23 (5): 385-392; Boswell et al., Chem. 21, 2153-2163 (2010). 10; Bumbaca Y. et al., 2015, J Biol Chem 290 (50): 29732-29741). The hypothesis is that the higher positive charge would lead to faster nonspecific clearance through increased nonspecific binding, possibly due to greater electrostatic interactions with the negatively charged extracellular matrix, whereas the lower positive charge would lead to decreased nonspecific binding and slower nonspecific clearance.

In order to understand effects of charge on transcytosis of mAbs, two sets of mAbs with designed Fv charge variants previously evaluated for PK behavior in several preclinical species (Bumbaca Y. et al., 2015, J Biol Chem 290 (50): 29732-29741) were tested in our assay. These charge variants were based on anti-lymphotoxin α (anti-LTα) and humAb4D5-8 (anti-HER2), with one for each parent antibody that had a more positively charged Fv (anti-LTα+3 and anti-HER2+3), and the other one had a less positively charged Fv (anti-LTα-4 and anti-HER2-4). In the reported study, both variants with more positive Fv charge showed faster nonspecific clearance whereas those with less positive charged showed similar or slower clearance compared to the parent molecule (Bumbaca Y. et al., 2015, J Biol Chem 290 (50): 29732-29741). The correlation between Fc charge and clearance was observed in all preclinical species tested including the cynomolgus monkey, mouse, and rat; the lack of species dependence supports the hypothesis of nonspecific electrostatic interaction between positively charged mAbs and negatively charged cellular components. As shown in Table 3, the order of transcytosis values of both set of charge variants follow the same trend as degree of Fv charge as well as the observed clearance rate in cynomolgus monkey. Compared to the parent molecules, both more positively charged variants (anti-LTα+3 and anti-HER2+3) showed higher transcytosis output whereas the two less charged molecules showed lower transcytosis output. It appeared that the transcytosis outputs correctly reflected the observed rank order of clearance rates of both sets of charge variants. Results of this study indicate that changes in charge of mAbs impact the transcytosis readout in our assay just as it does to their PK and that our assay is capable of reflecting charge impact on clearance.

TABLE 3

| mAb ID | Clearance in Cyno, mL/Kg/Day | Transcytosis, ng/mL | Fv Charge | pI |
|---|---|---|---|---|
| aLT − 4 | 5.78 | 3.8 | 4.1 | 9.01 |
| aLT | 14.9 | 6.0 | 8.1 | 9.43 |
| aLT + 3 | 59.3 | 16.0 | 11.1 | 9.61 |
| HCT − 4 | 6.63 | 3.2 | 2.1 | 8.83 |
| HCT | 6.22 | 2.7 | 6.1 | 9.27 |
| HCT + 5 | 51.1 | 20.5 | 11.1 | 9.65 |

Figures 5A, 5B, 5C:
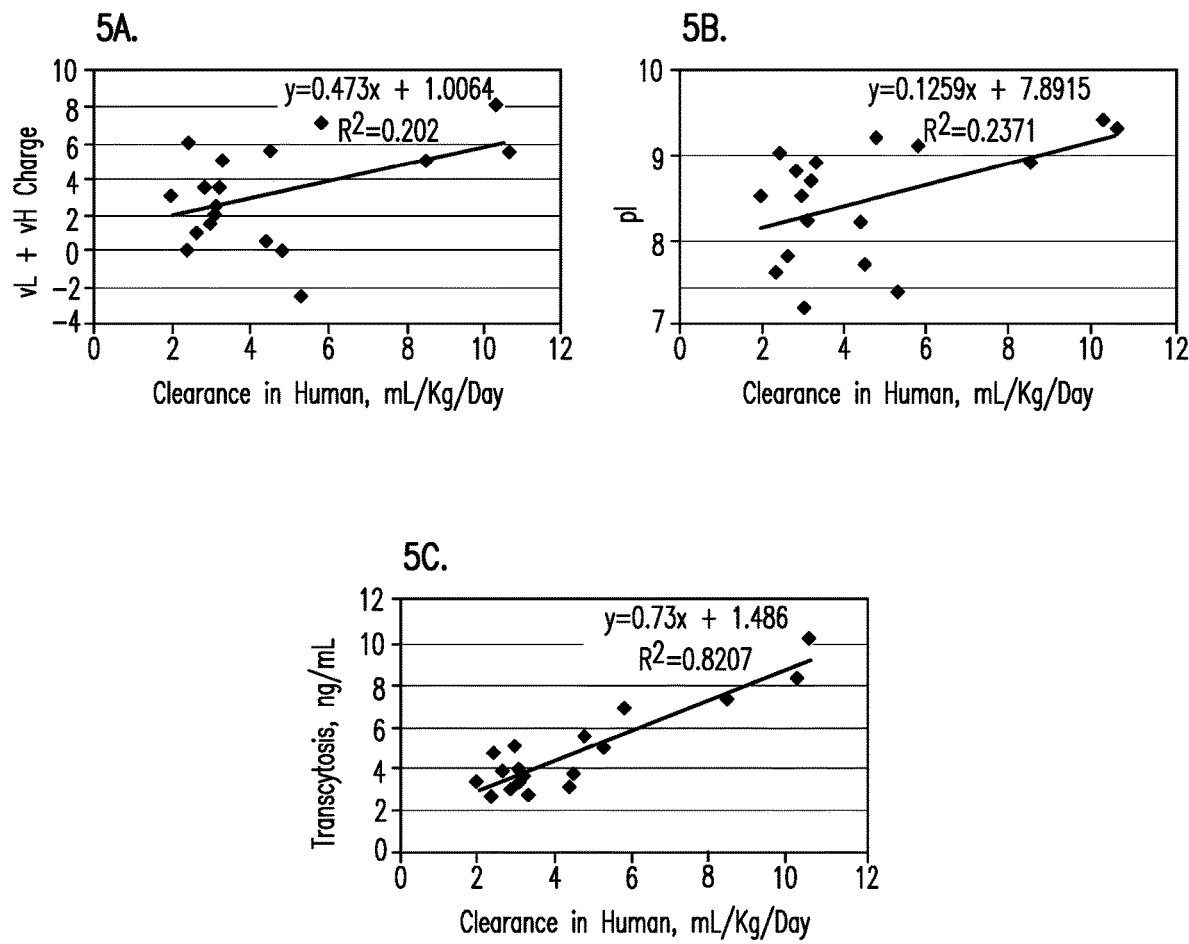
FIGS. 5A-5C show the relationships between clearance in human and either charge (FIG. 5A), pI (FIG. 5B), or the transcytosis output of the mAbs (FIG. 5C).
Figure 6:
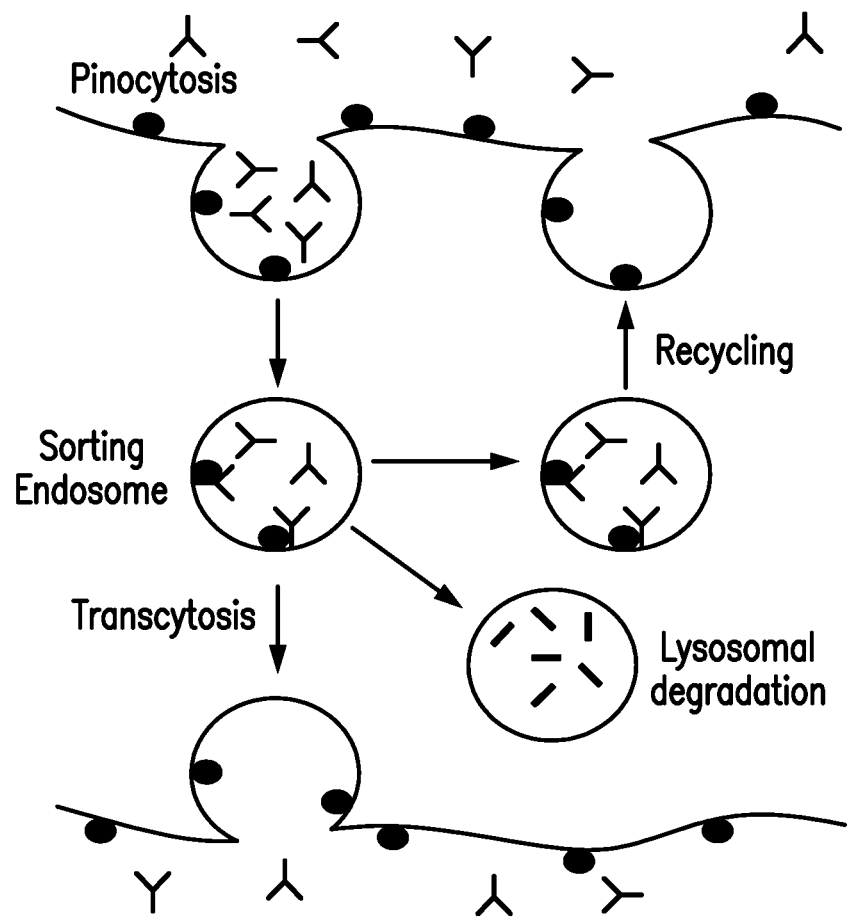
FIG. 6 depicts a schematic of potential fates of internalized molecules.

To better understand general impact of electrostatic interactions on clearance of mAbs in human, the combined Fv (vL+vH) charge of 19 mAbs (out of the 50 mAbs tested) were calculated and their correlations with clearance were analyzed. In addition, pI of these molecules was measured with icIEF and similar analysis was performed. As shown in FIGS. 5A and 5B, while a trend of association was observed between clearance rates in human and either pI or the combined Fv charge values, the strength of correlation appeared to be weak as evidenced by the relatively low R-squared value (less than 0.25). On the other hand, the correlation between clearance and transcytosis remains strong with this subset of mAbs (R-squared value greater than 0.8; FIG. 5C). It appears that while substantial alteration in charge is expected to modulate transcytosis behavior of mAbs, the output of this assay is determined by a combined effect contributed by multiple factors in addition to charge.

Example 5: Impact of Glycosylation on Transcytosis of Fc-containing molecules

Glycosylation patterns of mAbs or Fc-fusion proteins can significantly impact their PK and PD behaviors (Higel F. et al., 2016, Eur J Pharm Biopharm 100:94-100). It has been shown that mAbs carrying greater than 99% of high-mannose N-glycans (Man5 or Man8/9) showed faster clearance in preclinical species compared to controls with typical glycosylation pattern (Yu M et al., 2012, MAbs 4 (4): 475-487), and that Fc-fusion proteins with extensive sialylation in the fusion partner showed reduced clearance compared to their less sialylated counterparts (Stefanich E G et al., 2008 J Pharmacol Exp Ther 327 (2): 308-315). It is hypothesized that mAbs carrying high-mannose glycans are bound and cleared by mannose receptor most markedly expressed on immune cells (Lee S J et al., 2002, Science 295 1898-1901), while Fc-fusion proteins with exposed terminal galactose (without sialylation) are bound and cleared by the asialoglycoprotein receptor expressed in the liver (Stockert R J, 1995, Physiol. Rev. 75:591-609).

To investigate effects of glycosylation on transcytosis of mAbs and Fc-fusion proteins, two sets of molecules with variations in glycosylation patterns were tested. The variants of ocrelizumab ($2H_7$) glycoform include one without Fc N-linked glycan by in vitro deglycosylation ($2H_7$-DG) and the other carrying greater than 99% mannose 5 glycans ($2H_7$-Man5). The other set of variants is based on X-Fc, a fusion protein consisting of a human glycoprotein X and human IgG1 Fc; the 5 variants of X-Fc carry different levels of sialylation representing 1, 5, 8, 12, and 15 mole of sialic acid per mole of X-Fc (X-Fc1, X-Fc5, X-Fc8, X-Fc12, and X-Fc15, respectively). The clearance rates of $2H_7$ and $2H_7$-Man5 were obtained from a previously published study (Yu M et al., 2012, MAbs 4 (4): 475-487); the clearance rates of the X-Fc sialylation variants were generated from an in-house mouse study. While no clearance data was available for 2H7-DG, it has been reported that removal of Fc N-glycans does not induce discernible changes in their half-life (Tao MH and Morrison SL, 1989, J Immunol 143 (8): 2595-2601). In addition, atezolizumab which does not carry Fc N-glycans due to a N297G mutation shows a normal PK profile in human (Prescribing information and Table 1). As shown in Table 4, compared to 2H7, 2H7-DG showed similar transcytosis whereas 2H7-Man5 showed a 2-fold increase in transcytosis, the former predicts a similar clearance and the latter predicts a faster clearance, both of which are consistent with their expected/observed rank order for clearance rate in vivo. Similarly, the 5 X-Fc variants showed a decreasing level of transcytosis in an order consistent with decreased amount of exposed terminal galactose as a result of increased sialylation; the predicted rank order for clearance rates of these sialylation variants are consistent with the observed clearance data from the mouse study.

To investigate potential impact of glycosylation on FcRn binding and/or non-specific interactions with cells, both sets of glycosylation variants were tested for FcRn binding affinity and relative binding to MDCK-hFcRn cells. Compared to 2H7, the degycosylated molecule (2H7-DG) showed no discernible differences in binding to FcRn and the cells. On the other hand, the mannose-5 glycoform (2H7-Man5) showed a slight increase in binding to MDCK cells and a moderate increase in binding to FcRn at pH 6.0; however, it showed no increase in transcytosis in MDCK cells and no additional increase in binding to MDCK-FcRn cells. Similar to the 2H7 man-5 glycoform, the X-Fc sialylation variants showed no apparent correlation between transcytosis in MDCK-hFcRn cells and either binding to cells or transcytosis in MDCK cells. However, country to 2H7-Man5 which showed increased FcRn binding and increased transcytosis, the X-Fc sialylation variants showed a trend of increase in FcRn binding that inversely correlate with transcytosis outputs in MDCK-FcRn cells. It suggests that glycosylation may impact FcRn binding and transcytosis differently depending on the glycan species. Of note, the lack of an notable increase in binding to MDCK cells by 2H7-Man5 and X-Fc-SAI suggest that the increase in transcytosis was not due to binding to specific receptors such a mannose receptors or asialoglycoprotein receptors that known to involved in the in the catabolism of these IgG glycoforms; however, we have no direct evidence to confirm the presence or absence of such receptors in MDCK cells.

TABLE 4

| ID | Clearance, mL/Day/kg (mice) | Transcytosis (MDCK-hFcRN), ng/mL | Transcytosis (MDCK), ng/mL | FcRn binding at pH 6.0, μM | Binding to MDCK-hFcRN, MFI | Binding to MDCK, MFI |
|---|---|---|---|---|---|---|
| 2H7 | 9.89* | 4.8 | 0.5 | 0.45 | 140 | 105 |
| 2H7-DG | ND | 4.3 | ND | 0.44 | 160 | 129 |
| 2H7-Man5 | 27.1* | 10.3 | 0.5 | 0.23 | 207 | 157 |
| X-Fc-SA1 | 952.5 | 10.7 | 0.7 | 0.36 | 160 | 144 |
| X-Fc-SA5 | 401.8 | 8.1 | 0.6 | 0.29 | 473 | 183 |
| X-Fc-SA8 | 132.5 | 6 | 0.8 | 0.16 | 166 | 137 |
| X-Fc-SA12 | 42.6 | 4.3 | 0.9 | 0.11 | 157 | 151 |
| X-Fc-SA15 | 25.1 | 3.8 | 0.8 | 0.09 | 215 | 258 |

Example 6: Impact of Extreme FcRn Binding on Transcytosis of mAbs

Modifications of binding affinity toward FcRn via genetic engineering have been shown to impact the half-life of therapeutic antibodies and Fc-fusion proteins (Ward E S et al., 2015, Mol Immunol 67 (2 Pt A): 131-141). Thus, it is of interest to investigate transcytosis behavior of mAbs carrying engineered mutations for substantially altered FcRn binding affinity. Two sets of molecules were tested for transcytosis in both parental MDCK and MDCK-hFcRn cells. The first set includes anti-VEGF (a humanized IgG1 mAb), and anti-VEGF-QA which carries T307Q/N434A mutations that increase the FcRn binding by close to 10-fold (Yeung Y A et al., 2010, Cancer Res 70 (8): 3269-3277). The second set include a humanized herpes simplex virus glycoprotein D-specific IgG1 antibody, anti-gD (WT), and two of its FcRn binding variants, anti-gD-HAHQ which carries the H310A/H435Q mutations that diminish its FcRn binding activity to an undetectable level (Kenanova V. et al., 2005, Cancer Res 65 (2): 622-631), and anti-gD-YTE that carries the M252Y/S254T/T256E mutations which increase its FcRn binding for more than 10-fold (Dall'Acqua, 2006). As shown in Table 5, apparent transcytosis of all five molecules were clearly observed in MDCK-hFcRn cells with anti-gD-HAHQ showed the lowest transcytosis value, likely due to its inability to bind to FcRn. However, contrary to results from the mAb panel where increased transcytosis outputs correlate with increased clearance rates (fast clearance), both anti-VEGF-QA and anti-gD-YTE that exhibit slow clearance in vivo showed increased transcytosis compared to their wildtype counterparts. It is possible that molecules with extreme FcRn binding affinity might behave differently in this assay due to their differential responses toward the soring mechanisms governing recycling and transcytosis pathways.

Interestingly, while most of the molecules showed low level transcytosis in MDCK cells that were either below or barely above the detection limit of the ELISA at 0.3 ng/ml, anti-gD-YTE showed a notable transcytosis level at more than 1 ng/mL which presumably is independent of FcRn.

The substantial differences in transcytosis output observed between the two cell lines support that the observed transcytosis in MDCK-hFcRn cells is primary driven by FcRn and that the assay is specific to molecules that contain an intact Fc domain of IgG capable of interacting with FcRn. Of note, whereas both anti-VEGF-QA and anti-gD-YTE exhibit an 8-10 folds increase in FcRn binding activity compared to their wildtype counterparts, the increase in transcytosis was rather modest; less than two-fold for anti-VEGF-QA and slightly over two-fold for anti-gD-YTE.

TABLE 5

| mAb ID | Transcytosis (MDCK), ng/mL | Transcytosis (MDCK-hFcRn), ng/mL | FcRn binding, Kd (µM) |
|---|---|---|---|
| Anti-gD-WT | 0.3 | 3.0 | 1.01 |
| Anti-gD-HAHQ | <0.3 | 0.8 | Not Detectable |
| Anti-gD-YTE | 1.1 | 7.0 | 0.08 |
| Anti-VEGF | <0.3 | 3.4 | 2.4 |
| Anti-VEGF-QA | <0.3 | 5.1 | 0.24 |

All publications, patents and other references cited herein are incorporated by reference in their entirety into the present disclosure.

What is claimed is:

1. A method of determining the in vivo clearance of a monoclonal antibody, comprising:
    a) introducing the monoclonal antibody into a first of two chambers where the first chamber is separated from the second chamber by a monolayer of Madin-Darby canine kidney (MDCK) cells expressing a human neonatal Fc receptor (FcRn) heavy chain and a human beta-2-microglobulin, and wherein each of the first and second chambers has a physiological pH value of 7.4;
    b) measuring the number of monoclonal antibodies transcytosed from the first chamber to the second chamber; and
    c) determining the in vivo clearance of the monoclonal antibody based on the number of monoclonal antibodies measured.

2. The method of claim 1, wherein measuring the number of the monoclonal antibodies transcytosed comprises use of an enzyme-linked immunosorbent assay (ELISA), liquid-scintillation counting (LSC), quantitative PCR, or a fluorescence reader system.

* * * * *